(12) United States Patent
Tischendorf et al.

(10) Patent No.: US 10,792,488 B2
(45) Date of Patent: Oct. 6, 2020

(54) MINIMALLY INVASIVE IMPLANTABLE NEUROSTIMULATION SYSTEM

(71) Applicant: Medtronic, Inc., Minneapolis, MN (US)

(72) Inventors: Brad C. Tischendorf, Minneapolis, MN (US); Eric H. Bonde, Minnetonka, MN (US); Phillip C. Falkner, Minneapolis, MN (US); John E. Kast, Hugo, MN (US); Randy S. Roles, Elk River, MN (US); Erik R. Scott, Maple Grove, MN (US); Todd V. Smith, Shoreview, MN (US); Xuan K. Wei, Minnetonka, MN (US); Anthony M. Chasensky, St. Paul, MN (US); Michael J. Ebert, Fridley, MN (US); Shawn C. Kelley, Shoreview, MN (US); Gabriela C. Molnar, Blaine, MN (US); Richard T. Stone, Minneapolis, MN (US)

(73) Assignee: MEDTRONIC, INC., Minneapolis, MN (US)

(*) Notice: Subject to any disclaimer, the term of this patent is extended or adjusted under 35 U.S.C. 154(b) by 291 days.

(21) Appl. No.: 15/900,083

(22) Filed: Feb. 20, 2018

(65) Prior Publication Data

US 2018/0168564 A1    Jun. 21, 2018

Related U.S. Application Data

(63) Continuation of application No. 14/098,621, filed on Dec. 6, 2013, now Pat. No. 9,931,107.

(Continued)

(51) Int. Cl.
*A61B 17/00* (2006.01)
*A61N 1/02* (2006.01)
(Continued)

(52) U.S. Cl.
CPC .......... *A61N 1/02* (2013.01); *A61B 17/00234* (2013.01); *A61N 1/05* (2013.01);
(Continued)

(58) Field of Classification Search
CPC .......... A61N 1/02; A61N 1/36; A61N 1/3605; A61N 1/37247; A61N 1/3756;
(Continued)

(56) References Cited

U.S. PATENT DOCUMENTS

| 3,971,388 A | 7/1976 | Cowdery |
| 5,152,298 A | 10/1992 | Kreyenhagen et al. |

(Continued)

FOREIGN PATENT DOCUMENTS

| CN | 101522256 A | 9/2009 |
| CN | 101522260 A | 9/2009 |

(Continued)

OTHER PUBLICATIONS

International Search Report and Written Opinion of Counterpart International Application No. PCT/US2013/073524, dated Apr. 9, 2014, 11 pp.

(Continued)

*Primary Examiner* — Anh T Dang
(74) *Attorney, Agent, or Firm* — Patterson Thuente Pedersen, P.A.

(57) ABSTRACT

A neuromodulation therapy is delivered via at least one electrode implanted subcutaneously and superficially to a fascia layer superficial to a nerve of a patient. In one example, an implantable medical device is deployed along a superficial surface of a deep fascia tissue layer superficial to a nerve of a patient. Electrical stimulation energy is delivered to the nerve through the deep fascia tissue layer via implantable medical device electrodes.

26 Claims, 29 Drawing Sheets

Related U.S. Application Data

(60) Provisional application No. 61/777,949, filed on Mar. 12, 2013, provisional application No. 61/777,838, filed on Mar. 12, 2013, provisional application No. 61/777,824, filed on Mar. 12, 2013, provisional application No. 61/777,804, filed on Mar. 12, 2013, provisional application No. 61/777,787, filed on Mar. 12, 2013, provisional application No. 61/734,446, filed on Dec. 7, 2012, provisional application No. 61/734,436, filed on Dec. 7, 2012, provisional application No. 61/734,429, filed on Dec. 7, 2012, provisional application No. 61/734,425, filed on Dec. 7, 2012.

(51) Int. Cl.
*A61N 1/05* (2006.01)
*A61N 1/372* (2006.01)
*A61N 1/375* (2006.01)
*A61N 1/36* (2006.01)
*A61N 1/378* (2006.01)

(52) U.S. Cl.
CPC ......... *A61N 1/0551* (2013.01); *A61N 1/3605* (2013.01); *A61N 1/36007* (2013.01); *A61N 1/36057* (2013.01); *A61N 1/36067* (2013.01); *A61N 1/36071* (2013.01); *A61N 1/36139* (2013.01); *A61N 1/3727* (2013.01); *A61N 1/3754* (2013.01); *A61N 1/3756* (2013.01); *A61N 1/3787* (2013.01); *A61N 1/37205* (2013.01); *A61N 1/37223* (2013.01); *A61N 1/37235* (2013.01); *A61N 1/37247* (2013.01); *A61N 1/36021* (2013.01); *A61N 1/36053* (2013.01); *A61N 1/37211* (2013.01); *A61N 1/37518* (2017.08); *F04C 2270/0421* (2013.01)

(58) Field of Classification Search
CPC ............ A61N 1/36021; A61N 1/36017; A61N 1/057; A61N 1/0573; A61N 1/0502; A61N 1/05; A61N 1/059; A61N 1/0504; A61N 1/0492; A61N 1/0484; A61N 1/04
See application file for complete search history.

(56) References Cited

U.S. PATENT DOCUMENTS

| | | | |
|---|---|---|---|
| 5,603,730 | A | 2/1997 | Romkee |
| 6,051,017 | A | 4/2000 | Loeb et al. |
| 6,975,906 | B2 | 12/2005 | Rusin et al. |
| 7,054,692 | B1 | 5/2006 | Whitehurst et al. |
| 7,103,415 | B2 | 9/2006 | Probst et al. |
| 7,444,184 | B2 | 10/2008 | Boveja et al. |
| 7,460,913 | B2 | 12/2008 | Kuzma et al. |
| 7,467,014 | B2 | 12/2008 | Fuller et al. |
| 7,496,404 | B2 | 2/2009 | Meadows et al. |
| 7,860,570 | B2 | 12/2010 | Whitehurst et al. |
| 7,949,395 | B2 | 5/2011 | Kuzma |
| 7,991,483 | B1 | 8/2011 | Atanasoska et al. |
| 8,086,324 | B1 | 12/2011 | Vase |
| 8,989,861 | B2 | 3/2015 | Su et al. |
| 8,996,114 | B2 | 3/2015 | Soltis et al. |
| 9,398,901 | B2 | 7/2016 | Tischendorf et al. |
| 9,486,628 | B2 | 11/2016 | Christopherson et al. |
| 9,585,642 | B2 | 3/2017 | Dinsmoor et al. |
| 9,826,963 | B2 | 11/2017 | Scott et al. |
| 2003/0114905 | A1 | 6/2003 | Kuzma |
| 2004/0015205 | A1 | 1/2004 | Whitehurst et al. |
| 2005/0021119 | A1 | 1/2005 | Sage et al. |
| 2005/0092507 | A1 | 5/2005 | Marshall et al. |
| 2005/0251237 | A1 | 11/2005 | Kuzma et al. |
| 2006/0085041 | A1 | 4/2006 | Hastings et al. |
| 2007/0100383 | A1 | 5/2007 | Pastore et al. |
| 2007/0123923 | A1 | 5/2007 | Lindstrom et al. |
| 2007/0156204 | A1 | 7/2007 | Denker et al. |
| 2008/0058871 | A1 | 3/2008 | Libbus et al. |
| 2008/0086181 | A1 | 4/2008 | Amurthur et al. |
| 2009/0118778 | A1 | 5/2009 | Biggs, Jr. et al. |
| 2009/0149900 | A1 | 6/2009 | Moffitt et al. |
| 2009/0157147 | A1 | 6/2009 | Cauller et al. |
| 2009/0275956 | A1 | 11/2009 | Burnes et al. |
| 2009/0281605 | A1 | 11/2009 | Marnfeldt et al. |
| 2010/0023102 | A1 | 1/2010 | Spruit |
| 2010/0106223 | A1 | 4/2010 | Grevious et al. |
| 2010/0152808 | A1 | 6/2010 | Boggs, II |
| 2011/0301670 | A1 | 12/2011 | Gross et al. |
| 2012/0130398 | A1 | 5/2012 | Ackermann et al. |
| 2012/0303105 | A1 | 11/2012 | Askarinya et al. |
| 2014/0163579 | A1 | 6/2014 | Tischendorf et al. |
| 2014/0163580 | A1 | 6/2014 | Tischendorf et al. |
| 2016/0331978 | A1 | 11/2016 | Tischendorf et al. |

FOREIGN PATENT DOCUMENTS

| | | |
|---|---|---|
| CN | 101528303 A | 9/2009 |
| WO | 2004002572 A1 | 1/2004 |
| WO | 2009134466 A1 | 11/2009 |
| WO | 2010059096 A1 | 5/2010 |

OTHER PUBLICATIONS

International Preliminary Report on Patentability from International Application No. PCT/US2013/073524. dated Jun. 18, 2015. 8 pp
Prosecution History from U.S. Appl. No. 14/098,621, dated from Sep. 15, 2016 through Dec. 18, 2017, 80 pp.

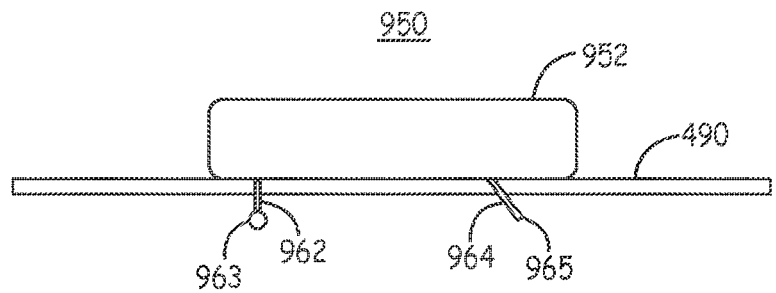
FIG. 39A
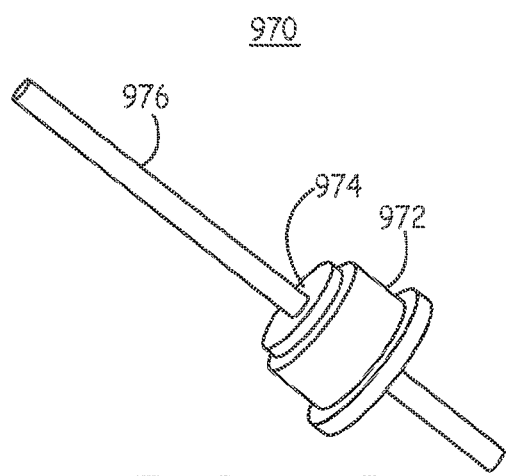
FIG. 39B
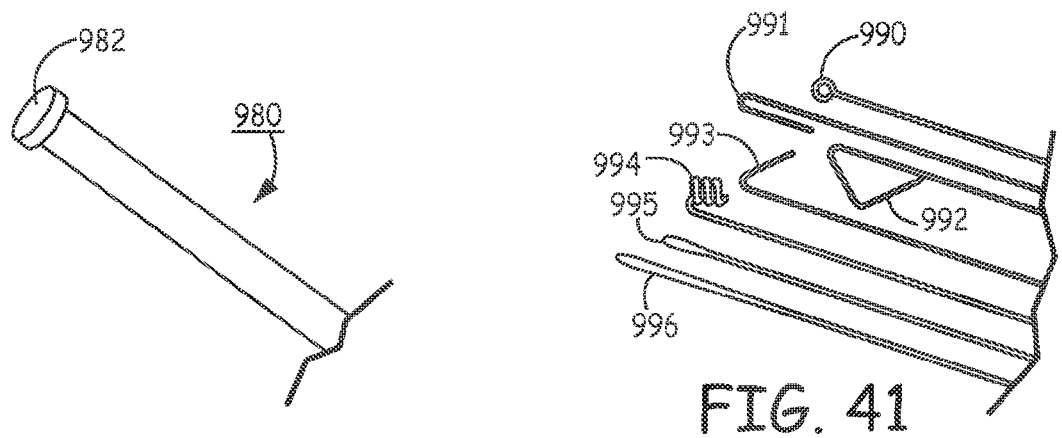
FIG. 40
FIG. 41

MINIMALLY INVASIVE IMPLANTABLE NEUROSTIMULATION SYSTEM

CROSS-REFERENCE TO RELATED APPLICATIONS

The present application is a continuation of U.S. patent application Ser. No. 14/098,621, filed Dec. 6, 2013, which application is incorporated herein by reference as if re-written in its entirety.

The present application claims the benefit of U.S. Provisional Patent Application No. 61/734,425, filed Dec. 7, 2012, which application is incorporated herein by reference as if re-written in its entirety.

The present application claims the benefit of U.S. Provisional Patent Application No. 61/777,804, filed Mar. 12, 2013, which application is incorporated herein by reference as if re-written in its entirety.

The present application claims the benefit of U.S. Provisional Patent Application No. 61/734,429, filed Dec. 7, 2012, which application is incorporated herein by reference as if re-written in its entirety.

The present application claims the benefit of U.S. Provisional Patent Application No. 61/777,949, filed Mar. 12, 2013, which application is incorporated herein by reference as if re-written in its entirety.

The present application claims the benefit of U.S. Provisional Patent Application No. 61/734,446, filed Dec. 7, 2012, which application is incorporated herein by reference as if re-written in its entirety.

The present application claims the benefit of U.S. Provisional Patent Application No. 61/777,824, filed Mar. 12, 2013, which application is incorporated herein by reference as if re-written in its entirety.

The present application claims the benefit of U.S. Provisional Patent Application No. 61/777,838, filed Mar. 12, 2013, which application is incorporated herein by reference as if re-written in its entirety.

The present application claims the benefit of U.S. Provisional Patent Application No. 61/734,436, filed Dec. 7, 2012, which application is incorporated herein by reference as if re-written in its entirety.

The present application claims the benefit of U.S. Provisional Patent Application No. 61/777,787, filed Mar. 12, 2013, which application is incorporated herein by reference as if re-written in its entirety.

The present application claims priority to U.S. Provisional Patent Application No. 61/777,787, filed Mar. 12, 2013, which application is incorporated herein by reference as if re-written in its entirety.

FIELD OF THE DISCLOSURE

The disclosure relates generally to implantable neurostimulation systems and in particular to minimally invasive neurostimulation systems.

SUMMARY

Various exemplary embodiments of a minimally invasive implantable medical device system deliver neurostimulation to a targeted nerve or neural tissue through a tissue layer. In one embodiment, a method for providing neuromodulation includes deploying an implantable medical device along a superficial surface of a deep fascia tissue layer superficial to a nerve of a patient and delivering electrical stimulation energy via electrodes coupled to the device to stimulate the nerve through the deep fascia tissue layer. In one example the nerve is the tibial nerve and the device is implanted along a superficial surface of a deep fascia tissue layer extending over the tibial nerve. Deploying the device may include dissecting a tissue pocket using a first end of a dissection tool and delivering test stimulation pulses using an electrode coupled to the first end of the dissection tool and electrically coupled to a pulse generator via a connector at a second end of the dissection tool to locate the tibial nerve. A second end of the dissection tool may include an incising blade for making a skin incision.

Deploying the implantable medical device may include positioning at least one electrode carried along a face of a housing of the implantable medical device against the tissue layer and/or advancing an electrical lead, carrying at least one electrode, along the tissue layer superficial to the tibial nerve. The method for providing the neuromodulation therapy may further include providing power from an external device positioned cutaneously over the implantable medical device for powering the generation of stimulation pulses delivered to the nerve via the plurality of electrodes.

Deploying the implantable medical device may further include fixating the implantable medical device along the tissue layer using a fixation member. A passive fixation member extending from a housing of the implantable medical device may be engaged in a surrounding tissue. In other examples, fixating the implantable medical device includes inserting an active fixation member into the tissue layer to capture the tissue layer between a housing of the implantable medical device and a portion of the active fixation member. Inserting an active fixation member into the tissue layer may include advancing the active fixation member through an aperture of a housing of the implantable medical device.

In one embodiment, a system for delivering a neuromodulation therapy includes an implantable medical device configured to be deployed along a superficial surface of a deep fascia tissue layer superficial to a nerve of a patient. The implantable medical device includes a housing, electrodes and a pulse generating circuit enclosed in the housing for delivering electrical stimulation pulses via the electrodes to the nerve through the deep fascia tissue layer. The system may further include a dissection tool having a first end for dissecting a tissue pocket and a second end comprising an electrical connector. The dissection tool may include an electrode coupled to the first end and electrically coupled to the connector; the connector adapted to be coupled to a pulse generator for delivering test stimulation pulses via the electrode coupled to the dissection tool to locate the nerve. The second end of the dissection tool may include an incising blade for making a skin incision.

In various embodiments, the implantable medical device system includes at least one electrode carried along a face of the housing of the implantable medical device configured to be positioned against the superficial surface of the tissue layer. Additionally or alternatively, the implantable medical device includes an electrical lead carrying at least one electrode adapted to be advanced along the superficial surface of the tissue layer. The system may include an external device for transmitting power from a cutaneous position over the implantable medical device for powering the pulse generator to generate stimulation pulses delivered to the nerve via the electrodes.

The system may further include a fixation member for fixating the implantable medical device along the superficial surface of the tissue layer. The fixation member may include a passive fixation member extending from a housing of the implantable medical device for engaging a surrounding tissue. Additionally or alternatively, the system of claim may include an active fixation member adapted to be inserted into the tissue layer for fixating the implantable medical device by capturing the tissue layer between the housing of the implantable medical device and a portion of the active fixation member. The housing may include an aperture for receiving the active fixation member, the active fixation member configured to be advanced through the aperture into the tissue layer.

In one exemplary embodiment, a method for delivering a neurostimulation therapy includes delivering electrical stimulation energy via at least one electrode positioned subcutaneously and superficially to a deep fascia tissue layer superficial to a tibial nerve to stimulate the tibial nerve through the deep fascia tissue layer.

BRIEF DESCRIPTION OF THE DRAWINGS

FIG. 28 is a perspective view of an exemplary IMD including a housing tethered to an elongated lead adaptor at an electrically insulated sealed electrical feed through.

FIG. 39A is a side view of an exemplary IMD including one or more electrodes embodied as feedthrough pins extending from IMD housing.

FIG. 39B is a perspective view of an exemplary feedthrough assembly.

FIG. 40 is an enlarged perspective view of an exemplary feedthrough pin.

FIG. 41 is a depiction of a variety of exemplary stamped or preformed feedthrough pins including variously shaped exemplary distal ends

DETAILED DESCRIPTION

Applicants have an appreciation that implantable medical device (IMD) technology is continually advancing as new applications are developed for automated therapy delivery in patients. Such advances may be further enhanced by using devices of reduced size and weight, which makes implantation of such devices less invasive and chronic use more comfortable for the patient. Additionally, applicants recognize that such enhancements such as improved power supply systems, wireless telemetry systems for communication with the implanted device, tools for performing implantation procedures, apparatus and methods for targeting a delivered therapy at a desired location, and other system improvements can also enhance therapies in a manner that saves cost, conserves energy and minimizes any burden placed on the patient or clinician. Accordingly, Applicants recognize a need for improved, minimally-invasive implantable medical device systems and associated methods of use for providing patient monitoring and/or therapy delivery. Certain exemplary embodiments disclosed herein may obtain some or all of the aforementioned advantages and enhancements.

When implanting small devices at targeted monitoring or therapy delivery locations, stable fixation of the device can be important, though not necessarily essential, in achieving effective therapy delivery and/or accurate monitoring of physiological signals. Stable fixation at a selected implant site can reduce power requirements of a device delivering an electrical stimulation therapy because therapy delivery electrodes can be positioned at an optimal location to deliver therapeutic pulses. Accordingly, Applicants recognize a need for improved, minimally-invasive implantable medical device systems and associated methods of use for providing stationary and/or ambulatory patient monitoring and/or therapy delivery.

In the following description, references are made to illustrative embodiments. Various embodiments of electrodes, fixation mechanisms and implant delivery tools for an IMD included in an implantable neurostimulation (INS) system for delivering an electrical stimulation therapy to a targeted neural site are described. However, it is recognized that the various embodiments described herein may be implemented in numerous types of IMDs, including, for example, implantable sensors or monitoring devices, implantable communication devices, and other types of implantable therapy delivery systems. The various embodiments of IMD systems described herein and associated methods of manufacture promote and facilitate minimally invasive implantation procedures in which the incision size and time required to implant and anchor the device can be minimized. The fixation mechanisms provide stable positioning of the IMD to promote efficient therapy delivery (and/or accurate monitoring in a sensing device).

Figure 1A:
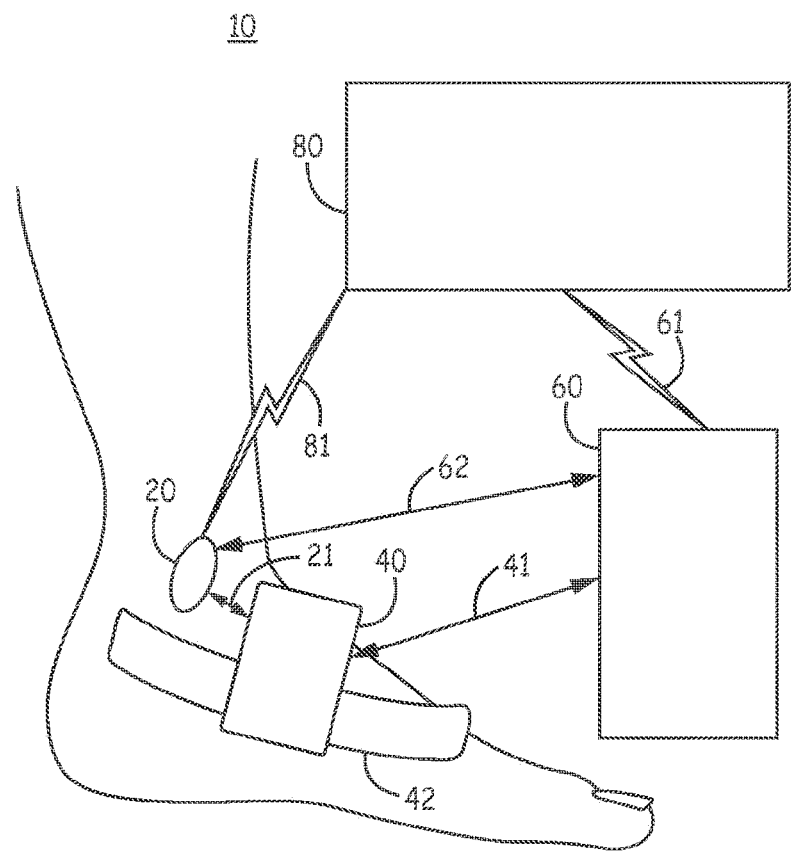
FIG. 1A is a schematic diagram of an exemplary minimally invasive IMD system capable of delivering a neurostimulation therapy.
Figure 1A:
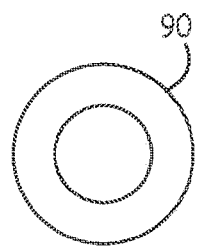

FIG. 1A is a schematic diagram of a minimally invasive INS system 10 capable of delivering a neurostimulation therapy. System 10 includes an IMD 20, an external device 40 enabled for transmitting signals to IMD 20, a patient programming device 60 enabled for bidirectional communication with IMD 20 and/or external device 40, and a physician programming device 80 according to an illustrative embodiment. In the illustrative embodiments described herein, communication between components included in the INS system 10 is configured to be bidirectional communication, however it is recognized that in some embodiments communication between two or more system components may be unidirectional.

IMD 20 includes circuitry for delivering neurostimulation pulses enclosed in a sealed housing and coupled to therapy delivery electrodes. In various embodiments, IMD 20 may include one or more of a primary battery cell, a rechargeable battery cell, and an inductively coupled power source for providing power for generating and delivering stimulation pulses and powering other device functions such as communication functions.

In some embodiments, IMD 20 is less than approximately 30 mm in length, or less than approximately 15 mm in length, and less than approximately 1 cc in volume. In illustrative embodiments, the term "approximately" as used herein may indicate a value of +10% of a stated value or may correspond to a range of manufacturing specification tolerances. In other examples, IMD 20 may be less than approximately 10 mm in length and may be less than approximately 0.6 cc in volume. IMD 20 may be approximately 0.1 cc in volume in some embodiments. The embodiments described herein are not limited to a particular size and volume of IMD 20, but are generally implemented to enable the use of a reduced size device for minimally invasive implantation procedures and minimized discomfort to a patient. It is recognized, however, that the various IMD systems described herein may be implemented in conjunction with a wide variety of IMD sizes and volumes adapted for a particular therapy or monitoring application.

External device 40 may be a wearable device including a strap 42 or other attachment member(s) for securing external device 40 to the patient in operable proximity to IMD 20. When IMD 20 is provided with rechargeable battery cell(s), external device 40 may be embodied as a recharging unit for transmitting power, for example inductive power transmission from external device 40 to IMD 20. In this embodiment, programming device 60 may be a patient handheld device that is used to initiate and terminate therapy delivered by IMD 20 via a bidirectional wireless telemetry link 62. Alternatively, programming device 60 could be operated by a patient for communicating with wearable external device 40 to control therapy on and off times and other therapy control parameters, which are transmitted to IMD 20 via communication link 21. Programming device 60 may communicate with wearable external device 40 via a bidirectional wireless telemetry link 41 that may establish communication over a distance of up to a few feet, enabling distance telemetry such that the patient need not position programming device 60 directly over IMD 20 to control therapy on and off times or perform other interrogation or programming operations (e.g., programming of other therapy control parameters).

When IMD 20 includes primary cell(s), a wearable external device 40 may be optional. Programming of IMD 20 may be performed by the programming device 60, using near- or distance-telemetry technology for establishing bidirectional communication link 62 for transmitting data between programmer 60 and IMD 20. Programming device 60 may be used by a patient or clinician to set a therapy protocol that is performed automatically by IMD 20. Programming device 60 may be used to manually start and stop therapy, adjust therapy delivery parameters, and collect data from IMD 20, e.g. data relating to total accumulated therapy delivery time or other data relating to device operation or measurements taken by IMD 20.

When IMD 20 is configured as an externally powered device, external device 40 may be a power transmission device that is worn by the patient during a therapy session to provide power needed to generate stimulation pulses. For example, external device 40 may be a battery powered device including a primary coil used to inductively transmit power to a secondary coil included in IMD 20. External device 40 may include one or more primary and/or rechargeable cells and therefore may include a power adaptor and plug for re-charging in a standard 110V or 220V wall outlet, for example.

It is contemplated that in some embodiments the functionality required for transmitting power to IMD 20 when IMD 20 is embodied as a rechargeable or externally powered device and for programming the IMD 20 for controlling therapy delivery may be implemented in a single external device. For example, power transmission capability of external device 40 and programming capabilities of patient programmer 60 may be combined in a single external device, which may be a wearable or handheld device.

Physician programming device 80 may include increased programming and diagnostic functionality compared to patient programming device 60. For example, physician programming device 80 may be configured for programming all neurostimulation therapy control parameters, such as but not limited to pulse amplitude, pulse width, pulse shape, pulse frequency, duty cycle, therapy on and off times, electrode selection, and electrode polarity assignments. Patient programming device 60 may be limited to turning therapy on and/or off, adjusting a start time of therapy, and/or adjusting a pulse amplitude without giving access to the patient to full programming functions such that some programming functions and programmable therapy control parameters cannot be accessed or altered by a patient.

Physician programming device 80 may be configured to communicate directly with IMD 20 via wireless, bidirectional telemetry link 81, for example during an office visit. Additionally or alternatively, physician programming device 80 may be operable as remote programming instrument used to transmit programming commands to patient programming device 60 via a wired or wireless communication network link 61, after which patient programming device 60 automatically transmits programming data to IMD 20 via bidirectional telemetry link 62 (or via wearable external device 40 and link 21).

In some embodiments, the patient may be provided with a magnet 90 for adjusting operation of IMD 20. For example, application of magnet 90 may turn therapy on or off or cause other binary or stepwise adjustments to IMD 20 operations.

While IMD 20 is shown implanted along a portion of the lower leg of a patient, IMD 20 could be implanted at numerous sites according to patient need and the particular medical application. In the illustrative embodiment, IMD 20 is provided for stimulating the tibial nerve of the patient to treat overactive bladder syndrome and is merely one example of the type of medical application for which INS system 10 may be used. In another example, IMD 20 may be implanted to deliver a stimulation therapy to muscles of the pelvic floor, such as periurethral muscles or the external uretheral sphincter for treating symptoms of urinary incontinence or overactive bladder syndrome. In other examples, IMD 20 may be deployed for delivering neurostimulation therapy to an acupuncture point for treatment of a symptom associated with the acupuncture point. IMD 20 may be implemented in an INS system for providing numerous types of neurostimulation therapies, such as for pain control, autonomic nervous system modulation, functional electrical stimulation, tremor, and more.

Figure 1B:
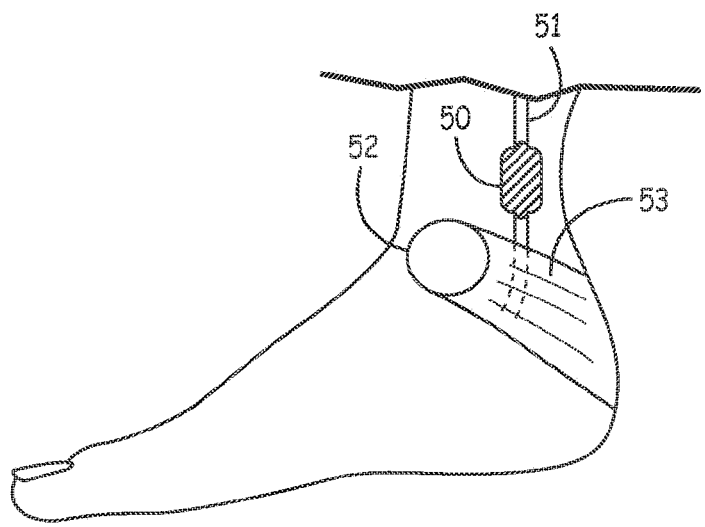
FIGS. 1B-1F are schematic illustrations depicting exemplary implant locations of an exemplary IMD system for delivering a neurostimulation therapy relative to a patient's anatomy.

FIGS. 1B-1F are schematic illustrations depicting implant locations of an IMD system for delivering a neurostimulation therapy relative to a patient's anatomy. FIG. 1B is a schematic illustration of a medial anatomical view of a portion of a foot and lower leg. The tibial nerve 51 is shown extending generally posterior relative to the medial malleolus 52. In one exemplary embodiment, the implant location of an IMD 50 for delivering a neurostimulation therapy to the tibial nerve 51 is superficial to the tibial nerve 51 slightly cephalad to the medial malleolus 52 and superior to the flexor retinaculum 53.

Figure 1C:
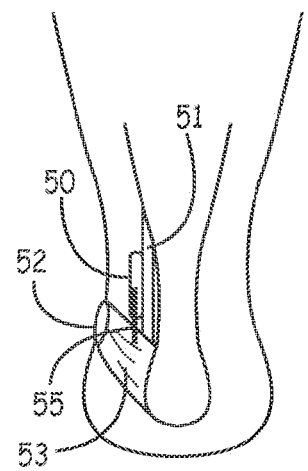

FIG. 1C is a schematic illustration of a posterior anatomical view of a portion of a foot and lower leg. The tibial nerve 51 extends posteriorly to the medial malleolus 52 and extends beneath the flexor retinaculum 53. In one embodiment, the implant location of the IMD 50 is over the tibial nerve slightly cephalad to the medial malleolus. The IMD 50 may be positioned along a superficial surface of a deep fascia tissue layer that extends superficially to the tibial nerve 51. In some embodiments as further described herein, the IMD 50 may be coupled to a lead 55 that may extend superficially to or deeper to a tissue layer superficial to the tibial nerve 51. For example, a lead 55 may extend through a deep fascia tissue layer to promote fixation of IMD 50 and lead 55 and position electrodes near the tibial nerve 51.

Figure 1D:
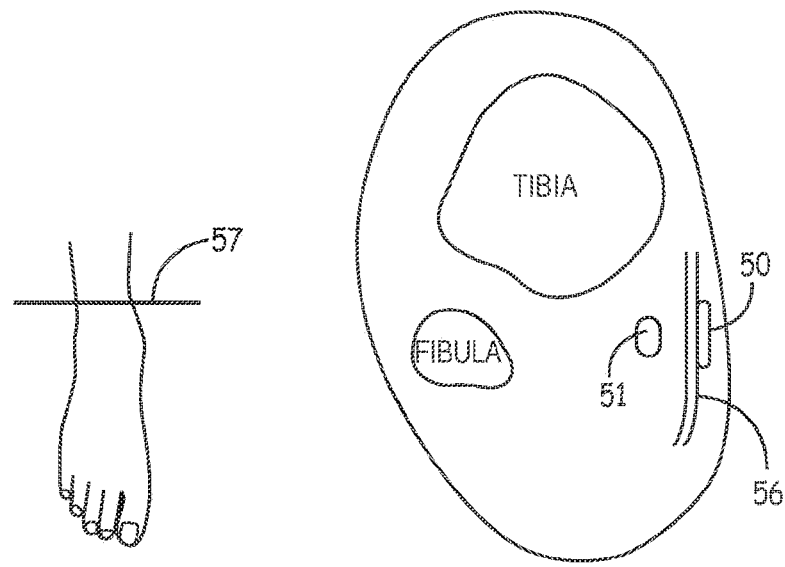

FIG. 1D is a schematic illustration of sectional anatomical view along a section line 57 in the distal third of a lower right leg slightly cephalad to the medial malleolus. In one exemplary embodiment, a minimally invasive IMD 50 is implanted superficial to the deep fascia 56. In another exemplary embodiment, the minimally invasive IMD 50 is implanted and secured superior to the retinaculum, along a deep fascia tissue layer. As shown in FIG. 1D, IMD 50 may be positioned against a superficial surface of fascia tissue layer 56, which extends superficially to tibial nerve 51. Neurostimulation therapy is delivered through the tissue layer 56.

Figure 1E:
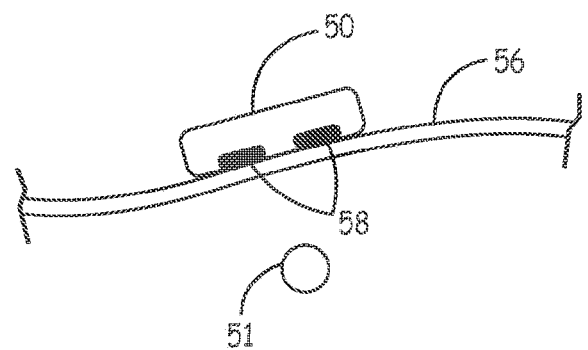

FIG. 1E is a schematic diagram of an IMD 50 positioned superficial to a deep fascia tissue layer 56 that extends superficially to a nerve, e.g. the tibial nerve 51. In some exemplary embodiments, the minimally invasive IMD 50 is implanted superficial to the deep fascia near the tibial nerve and stimulation is delivered through the deep fascia by electrodes 58 incorporated along the IMD housing positioned against the superficial surface of tissue layer 56. In other exemplary embodiments, as will be described herein, an electrode portion of the IMD penetrates through a small opening in the deep fascia, and the power generating portion of the IMD 50 is located superficial to the deep fascia.

Figure 1F:
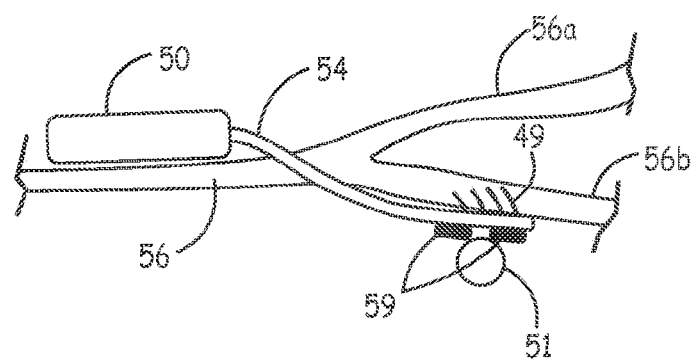

FIG. 1F is a schematic illustration of an anatomical variation in the vicinity of the tibial nerve 51. Deep fascia layer 56 bifurcates into a deep fascia layer 56a and the flexor retinaculum 56b. The deep fascia layer 56a extends superficially to the Achille's tendon (not shown) and the flexor retinaculum 56b. The flexor retinaculum 56b extends beneath, i.e. relatively deeper to, the Achilles tendon and over (superficially to) the tibial nerve. An IMD 50 may be positioned superficially to deep fascia layer 56. In some embodiments, an electrode portion of an IMD system may extend through the fascia layer 56 to position electrodes in closer proximity to the nerve 51 to reduce the simulation energy required to provide a therapeutic benefit. In the example shown, an IMD 50, including a housing enclosing IMD circuitry, is positioned superficially to fascia layer 56 and an electrical lead 54 coupled to IMD 50 extends through layer 56 to extend beneath the retinaculum 56b. Lead 54 carries electrodes 59 positioned in proximity to tibial nerve 51. In other embodiments, both IMD 50 and lead 54 extend superficially to deep fascia 56 and 56a and deliver neurostimulation energy through any of deep fascia layer 56, layer 56a and retinaculum 56b.

Advancement of lead 54 through deep fascia layer 56 promotes anchoring of IMD 50 at the implant site. Lead 54 may include fixation members 49 to further promote anchoring of IMD 50 and fixation of lead 54 at the therapy delivery site. Fixation members 49 are shown as passive fixation members, such as tines or barbs, which extend from lead 54 and passively engage in surrounding tissue without being actively fixed in the surrounding tissue at the time of implant. Fixation members 49 are shown schematically in FIG. 1F to extend from a relatively distal portion of lead 54 but may extend from any portion of lead 54 in any general direction (not necessarily toward the retinaculum 56b as depicted in the view of FIG. 1F). For example, the fixation members 49 may extend in a plane generally parallel to and beneath the retinaculum 56b. Other positions of passive fixation members are described below. While not shown explicitly in FIGS. 1E and 1F, passive fixation members 49 may additionally or alternatively extend from a portion of the housing of IMD 50, for example along lateral sidewalls of the IMD housing to contribute to the fixation of IMD 50 along a superficial surface of tissue layer 56.

As described in detail herein, various embodiments an IMD system deployed in various implant positions, e.g. as shown in FIGS. 1B through 1F, can include securing the IMD without piercing the deep fascia or another tissue layer, for example using passive fixation members engaging surrounding tissue. In other exemplary embodiments, the IMD can be secured by suturing to the deep fascia or another tissue layer or by fixation members that pierce the deep fascia for actively fixing the IMD location. The minimally invasive IMD signal generating portion may be located superficial to the deep fascia near the tibial nerve (or another targeted nerve) and one or more stimulating electrodes delivering an IMD generated signal (e.g. stimulation pulses) pierce or pass through the deep fascia, allowing the stimulating electrode to be located near or adjacent the tibial nerve (or another targeted nerve).

Figure 2:
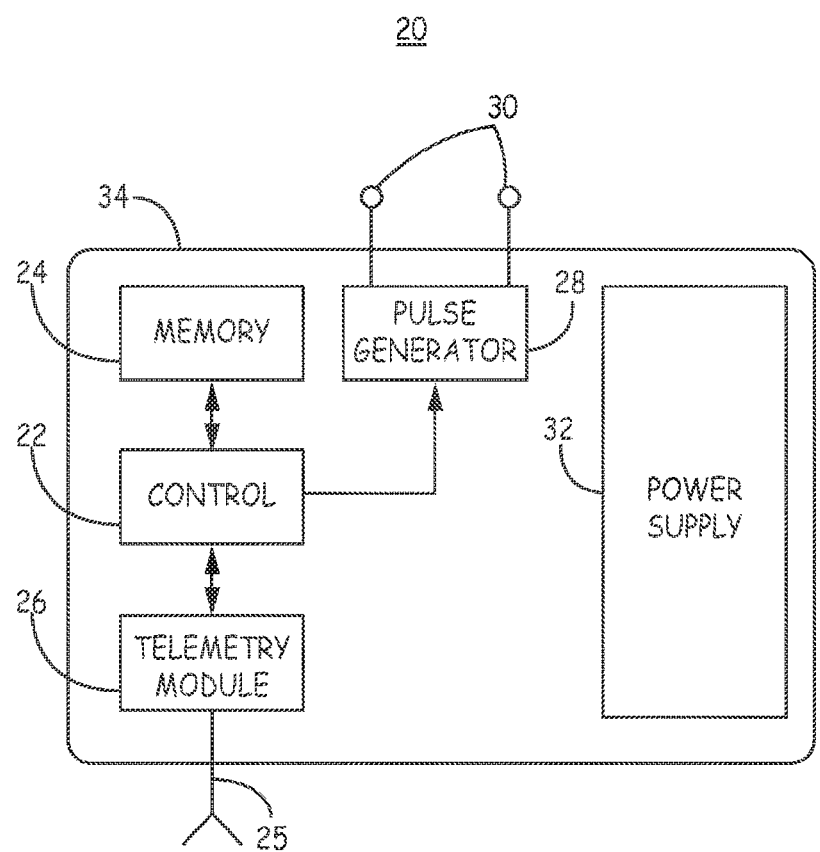
FIG. 2 is a functional block diagram of the IMD shown in FIG. 1A according to one exemplary embodiment.

FIG. 2 is a functional block diagram of IMD 20 of FIG. 1A according to one embodiment. IMD 20 includes a housing 34 enclosing a control unit 22 and associated memory 24, a telemetry module 26, and a pulse generator 28 coupled to electrodes 30. IMD 20 includes a power supply 32, which as described above may include any of a primary battery cell, a rechargeable battery cell, and/or a secondary coil of an externally powered system.

Control unit 22 may include any one or more of a microprocessor, a controller, a digital signal processor (DSP), an application specific integrated circuit (ASIC), a field-programmable gate array (FPGA), or equivalent discrete or integrated logic circuitry. In some examples, control unit 22 may include multiple components, such as any combination of one or more microprocessors, one or more controllers, one or more DSPs, one or more ASICs, or one or more FPGAs, as well as other discrete or integrated logic circuitry. The functions attributed to control unit 22 herein may be embodied as software, firmware, hardware or any combination thereof. In one example, a neurostimulation therapy protocol may be stored or encoded as instructions in memory 24 that are executed by controller 22 to cause pulse generator 28 to deliver the therapy via electrodes 30 according to the programmed protocol.

Memory 24 may include computer-readable instructions that, when executed by controller 22, cause IMD 20 to perform various functions attributed throughout this disclosure to IMD 20. The computer-readable instructions may be encoded within memory 24. Memory 24 may comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory, propagating signal.

Telemetry module 26 and associated antenna 25 are provided for establishing bidirectional communication with wearable external device 40, patient programmer 60 and/or physician programmer 80. Examples of communication techniques used by IMD 20 and a programming device 60 or 80 include low frequency or radiofrequency (RF) telemetry, which may be an RF link established via Bluetooth, WiFi, or MICS, for example. Antenna 25 may be located within, along or extend externally from housing 34.

Electrodes 30 may be located along an exterior surface of housing 34 and are coupled to pulse generator 28 via insulated feedthroughs or other connections as will be further described below. In other embodiments, electrodes 30 may be carried by a lead or insulated tether electrically coupled to pulse generator 28 via appropriate insulated feedthroughs or other electrical connections crossing sealed housing 34. In still other embodiments, electrodes 30 may be incorporated in housing 34 with externally exposed surfaces adapted to be operably positioned in proximity to a targeted nerve and electrically coupled to pulse generator 28.

Figure 3:
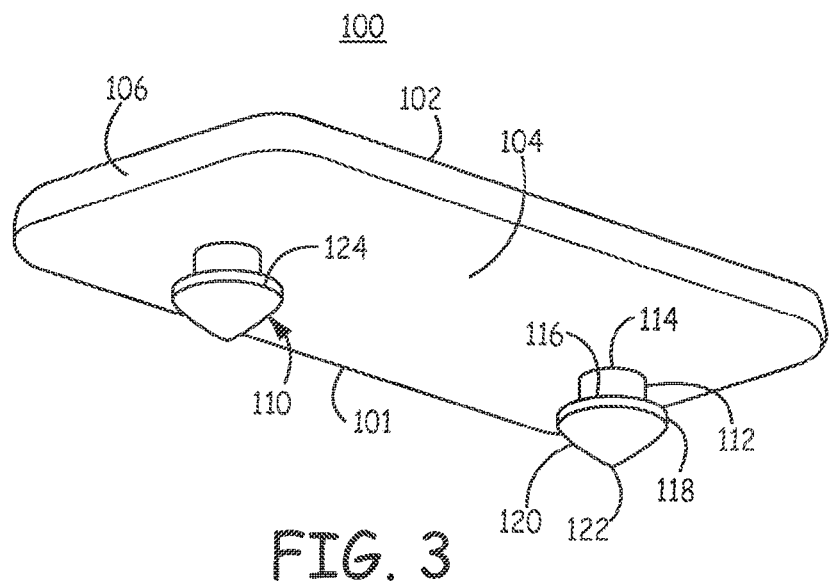
FIG. 3 is a perspective view of an exemplary IMD that may be included in an INS system according to one embodiment.

FIG. 3 is a perspective view of an IMD 100 that may be included in an INS system according to one embodiment. IMD 100 includes a sealed housing 101 having a generally flat profile for positioning between tissue layers. Housing 101 includes a top face 102 separated from a bottom face 104 by sidewall 106. Housing 101 further includes one or more fixation members 110. Housing fixation members 110 each include a post 112 extending between a proximal end 114 fixed to housing bottom face 104 and a distal end 116 extending away from housing face 104. Post 112 is shown having a circular cross section, but may have other cross-sectional shapes in other embodiments. In some embodiments, post 112 is a solid member, and in other embodiments post 112 is a hollow member, defining an inner lumen.

Post 112 has a flange 118 at or near distal post end 116. Post 112 and flange 118 may be a single component formed of a biostable polymer or as two components bonded together to form a flanged post. In alternative embodiments, post 112 and flange 118 may be a single component formed of or layered with a conductive electrode material, such as titanium, platinum, iridium, niobium or alloys thereof. The post 112 and flange 118 may then function both as an electrode for delivering a neurostimulation therapy and a fixation member.

In other embodiments, flange 118 may be formed of a different material than post 112. Flange 118 may be formed of an electrically conductive biostable material, such as those listed above, and function as an electrode. Post 112 may be formed from a biostable polymer, ceramic, or other non-conductive material. Post 112 may include an inner lumen through which a conductor extends, or a conductor may be solidly embedded within post 112, to electrically couple flange 118 to circuitry within housing 101. Alternatively, post 112 may be an electrically conductive material and function as an electrode, and flange 118 may be a non-conductive material, such as a polymer or a ceramic.

As shown in FIG. 3, post 112 is terminated by a puncture tip 120, distal to flange 118. Puncture tip 120 includes a proximal surface 124 configured to mate with flange 118 and may be fixedly attached to flange 118 at a joint between flange 118 and proximal surface 124. Puncture tip 120 has a distal sharpened tip 122 for puncturing through a tissue layer to advance post 112 and flange 118 through the tissue layer.

In some applications, puncture tip 120 is used to advance flange 118 through a relatively tough fibrous tissue layer, such as fascia, tendon, ligament, retinaculum, scar or other connective tissue. For example, in an application for treating overactive bladder syndrome, IMD 100 is implanted in the vicinity of the tibial nerve to deliver neurostimulation to the tibial nerve. Fixation members 110 are used to secure IMD 100 over the nerve. Puncture tip 120 is punched through a deep fascia tissue layer extending over the tibial nerve so that flange 118 becomes positioned on one side of the tissue layer and IMD housing 101 is positioned on the other side of the tissue layer. Post 112 extends through the tissue layer. The flange 118 holds the IMD 100 in place over the deep fascia tissue layer near the nerve. When flange 118 and/or post 112 are formed from conductive material to operate as electrodes, these electrodes are positioned in close proximity to the tibial nerve, under the tissue layer, such that stimulation does not need to occur through the tissue layer, which could require relatively higher stimulation pulse energy.

Figure 4:
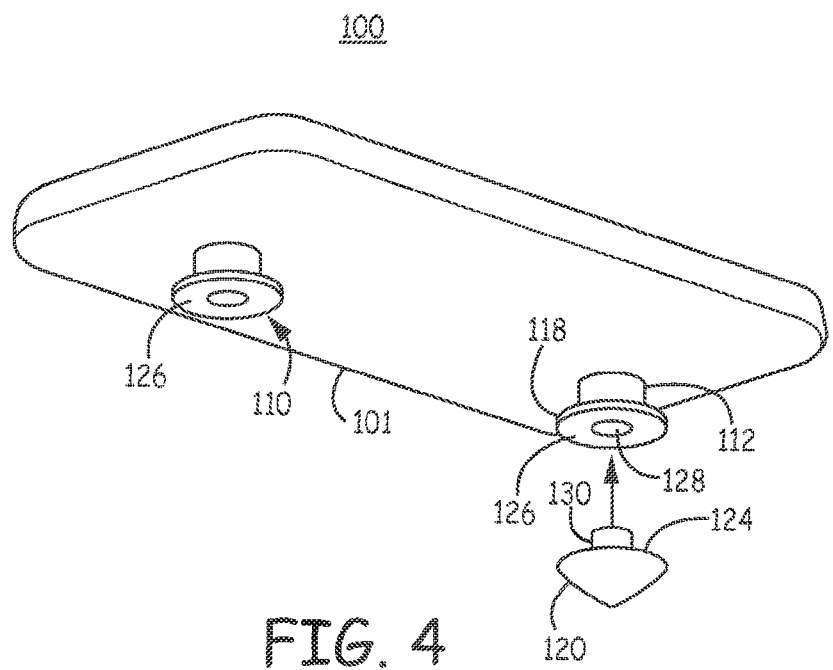
FIG. 4 is a perspective view of the IMD shown in FIG. 3 after exemplary puncture tips are removed.

FIG. 4 is a perspective view of IMD 100 shown in FIG. 3 after puncture tips 120 are removed. In one embodiment, puncture tips 120 are formed from a bioabsorbable or dissolvable material such that over time tips 120 are removed, leaving post 120 and flange 118 remaining. Flanges 118 remain as a fixation member retaining IMD 100 against the deep fascia, or other tissue layer, through which posts 112 have been advanced. Posts 112 limit movement of IMD 100 in x- and y-axes and flange 118 limits movement of IMD 100 in a z-axis. In this way, fixation members 110 limit movement of IMD 100 in all directions. In the time it takes for puncture tips 120 to be absorbed or dissolved, fibrotic encapsulation of IMD 100 will have occurred, which may further maintain the IMD in a stable position.

As mentioned previously, post 112 and flange 118 may define an inner lumen 128 for receiving a male connector 130 of puncture tip 120. Connector 130 may be press fit into lumen 128. In other embodiments, flange 118 and post 112 may be solid and puncture tip 120 may be adhesively coupled to flange 118.

In some embodiments, post 112, flange 118 and puncture tip 120 may be manufactured as a single component from a bioabsorbable or dissolvable material such that the entire fixation member 110 is absorbed or dissolved over time, during which fibrotic encapsulation of IMD 100 takes place. In still other embodiments, puncture tip 120 and flange 118 may be absorbable or dissolvable such that over time only post 112 remains to enable easier IMD removal than when flange 118 remains.

As indicated previously, all or any portion of post 112 and flange 118 may function as an electrode. In the embodiment shown in FIG. 4, for example, the distal surface 126 of flange 118 may function as an electrode. When two fixation members 110 are provided as shown, one of the flange surfaces 126 may function as the cathode and the other of the flange surfaces 126 may function as an anode. In other embodiments, one or more flange surfaces 126 of one or more fixation members 110 and/or other portions of fixation members 110 may be electrically tied together to form an active cathode while the housing 101 functions as the anode. Housing 101 may carry one or more electrodes (not shown in FIGS. 3 and 4) that may be selected in combination with each other or with any portion of fixation members 110 to provide electrically active surfaces for delivering a neurostimulation therapy.

Posts 112 may be attached to housing 101 on the outer bottom face 104 by fixedly coupling posts 112 at desired spacings along housing 101, using welding, brazing, adhesive bonding or other techniques. Alternatively, posts 112 may extend through housing 101 and be anchored to an inner surface of bottom face 104, e.g. by a flange, by varying outer diameters of post 112 mating with varying diameters of an opening through the wall of housing 101 and/or welded, brazed, or adhesively bonded to an inner surface of bottom face 104. Post 112 may function as insulation and sealing around an electrical feedthrough extending through bottom face 104 to enable electrical connection of flange 118 to circuitry within housing 101.

Figure 5:
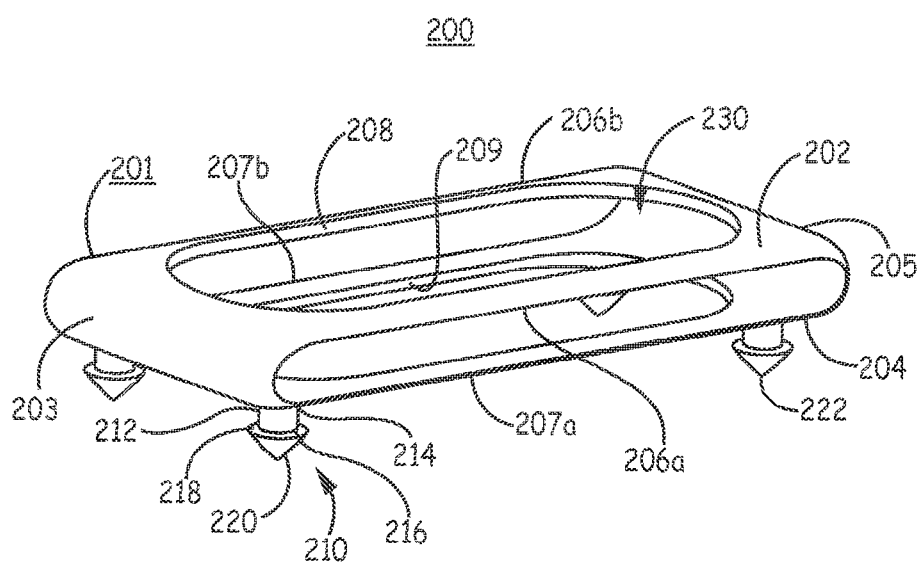
FIG. 5 is a perspective view of an exemplary fixation shroud according to an illustrative embodiment.

FIG. 5 is a perspective view of a fixation shroud 200 according to an illustrative embodiment. Rather than coupling fixation members directly to an IMD housing, fixation members may extend from a shroud sized to snugly surround the IMD. Shroud 200 includes a shroud body 201 and at least one housing fixation member 210 extending from the body 201. In the embodiment shown, shroud 200 includes four spaced apart fixation members, which may correspond to each of four corners of a face of an IMD.

Body 201 includes a top face 202 and bottom face 204 separated by opposing end side walls 203 and 205. Outer lateral edges 206a, 206b (collectively 206) of top face 202 and outer lateral edges 207a, 207b (collectively 207) of bottom face 204, respectively, define open lateral sides of shroud body 201. The open lateral sides defined by outer lateral edges 206 and 207 extend between opposing end side walls 203 and 205.

Each of top face 202 and bottom face 204 are shown having inner edges 208 and 209 defining an opening extending along the respective top and bottom face 202 and 204. Inner edges 208 and 209 may be configured as needed to expose surfaces of the IMD housing as desired, e.g. to expose electrodes carried on or incorporated in the IMD housing, expose a lead connector or other otherwise providing access to features of the IMD. Inner edges 208 and 209 may define openings to reduce the material required to manufacture shroud 200 and, when manufactured from a bioabsorbable or dissolvable material, reduces the volume of material that is absorbed or dissolved.

Fixation members 210 extend from shroud body 201. In one embodiment, fixation members 210 extend substantially perpendicular to shroud body face 204 to urge the IMD retained within cavity 230 defined by shroud body 201 against a tissue through which fixation members 210 extend. The fixation members 210 include posts 212 extending from a proximal end 214 at bottom face 204 to a distal end 216 extending away from shroud 200. A flange 218 extends radially outward at distal end 216, substantially parallel to bottom face 204. Post 212 terminates in a puncture tip 220 having a sharpened tip 222 for puncturing through a tissue layer to advance flange 218 through the tissue layer. The fixation member 210 will extend through a tissue layer such that shroud body 201 remains on one side of a tissue layer and flange 218 is positioned within or on the opposite side of the tissue layer.

In one embodiment, shroud 200, or at least a portion thereof, is a bioabsorbable or dissolvable component that will be fully absorbed or dissolved over time. Tissue encapsulation of the IMD replaces shroud 200 in limiting movement or migration of the IMD after shroud 200 is absorbed. Examples of bioabsorbable materials for use in fixation members described herein include copolymers of poly-lactic acid and poly-glycolic acid however any bioabsorbable polymer material could be used.

In other embodiments, only puncturing tip 220 is formed of a bioabsorbable or dissolvable device such that flanged posts 212 and shroud body 201 remain after puncturing tip 220 is absorbed. Flanged post 212 and shroud body 201 may be molded as one or more parts from a biostable polymer, such as a high durometer polyurethane, polyether ether ketone, or polysulfone to provide the column strength needed to puncture tips 222 through a tissue layer.

The shroud 200 may be an overmolded component in which the IMD is positioned in a mold and shroud 200 is molded onto and around the IMD. Alternatively, shroud 200 may be pre-molded of a generally rigid material in which an IMD is inserted into and retained in cavity 230.

Figure 6:
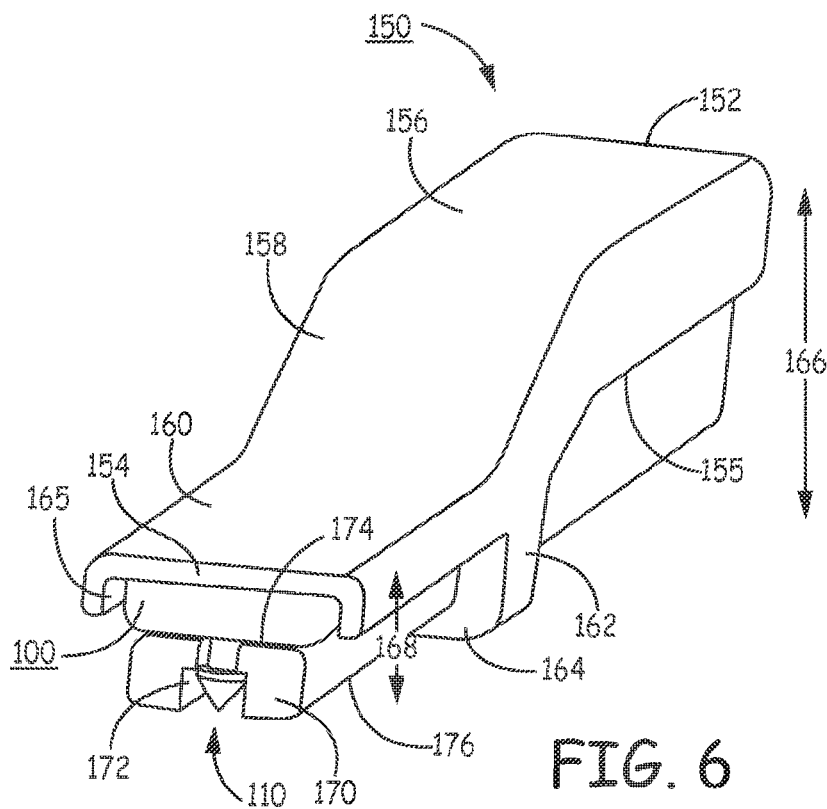
FIG. 6 is a perspective view of an exemplary implantation tool adapted for use with the IMD shown in FIG. 3.

FIG. 6 is a perspective view of an implantation tool 150 adapted for use with IMD 100 shown in FIG. 3. Tool 150 includes a tool body extending between a proximal end 152 and a distal end 154. The distal end 154 is a leading end inserted into a surgical pocket for implantation of IMD 100. The body of tool 150 includes a proximal portion 156 extending from proximal end 152, a distal portion 160 extending proximally from distal end 154, and a mid-portion 158 extending between the proximal portion 156 and the distal portion 160. Mid-portion 15 optionally extends at an angle between proximal portion 156 and distal portion 160. In one embodiment proximal portion 156 and distal portion 160 extend approximately parallel to each other with mid-portion 158 extending at an angle therebetween. The angled mid-portion 158 may provide comfortable ergonomic use of tool 150 and may be provided at different angles in other embodiments.

A bracket 162 extends from a bottom surface 155 of tool 150 for receiving an IMD retaining sleeve 170. Distal portion 160 is characterized by a relatively lower profile than proximal portion 156 in one embodiment such that distal portion 160 can be advanced into an open incision for implantation of IMD 100 while minimizing the size of the incision and the size of the pocket formed for IMD 100. As such, proximal portion 156 is shown having a height 166 from a bottom surface 164 of bracket 162. Distal portion 160 has a smaller height 168 from bracket bottom surface 164 than height 166. Proximal portion 156 has a thickness or height 166 and overall length to provide comfortable gripping of tool 150 by a physician, whereas distal portion 160 may be provided with a relatively smaller height for advancing through an incision and tunneling to an implant site and an overall length needed to reach a desired implant site from the incision site.

The distal portion 160 includes a bottom recessed surface 165 for receiving IMD 100. IMD retaining sleeve 170 extends through bracket 162 to distal tool end 154 to secure IMD 100 between recessed surface 165 and a top surface 174 of sleeve 170. Sleeve 170 includes one or more grooves 172 aligned with fixation member(s) 110 of IMD 100. In this way, sleeve 170 retains IMD 100 within tool 150 while protecting the puncturing tip of fixation member 110. Sleeve 170 extends proximally toward proximal end 152 and may extend fully to proximal end 152. Sleeve 170 may have varying heights such that top surface 174 mates with bottom surface 155 of tool 150.

During an implantation procedure, the distal portion 160 is advanced through an incision to position IMD 100 over a desired implant site. In some embodiments, distal end 154 may include a sharpened edge for incising or a relatively more blunt edge for dissecting and creating a tissue pocket within which IMD 100 is positioned. An incising edge may be provided as an attachable/detachable member or a retracting member for making a skin incision and when removed or retracted a relatively more blunt pocket dissection edge remains along end 154. Alternatively, tool 150 may include a blade cover or guard to be positioned over an incising edge to cover the incising edge when not in use. The blade cover or guard may have a blunt dissecting edge to form a tissue pocket. In other embodiments, edges of tool 150 are blunt or smooth to prevent trauma and provide comfortable gripping by a physician.

After positioning an IMD over a desired implant site, the sleeve 170 is withdrawn proximally by sliding sleeve 170 through bracket 162 in a proximal direction. As will be further described below, in some embodiments tool 150 and other delivery tools described herein may include nerve locating electrodes for identifying a nerve location prior to fixation of IMD 100 at an implant site. For example, an electrode bipole may be formed along a bottom surface of retaining sleeve 170 and coupled to insulated conductors extending within or along sleeve 170 to enable electrical connection to an external pulse generator. Test stimulation pulses may be delivered via the nerve locating electrodes as the position of IMD 100 is adjusted until a desired response is measured or observed. Upon identifying an optimal implant location, IMD 100 may be fixed at the implant site.

Figure 7:
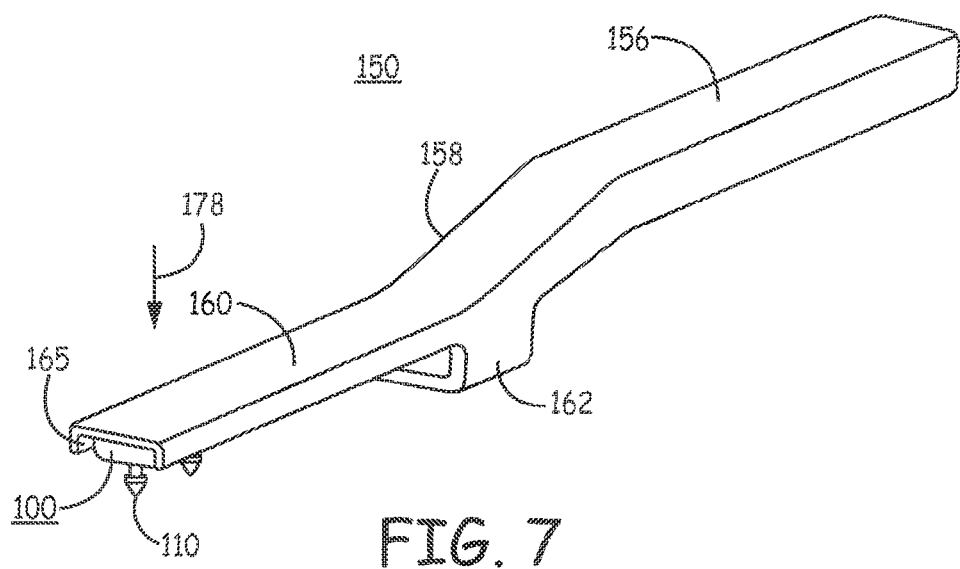
FIG. 7 is a perspective view of the implantation tool of FIG. 6 after removing IMD from a retaining sleeve.

FIG. 7 is a perspective view of implantation tool 150 after removing IMD retaining sleeve 170. IMD 100 remains within recess 165 of distal portion 160, but fixation members 110 are now exposed. IMD 100 is passively retained within recess 165 within the tissue pocket. Pressure is applied along a top surface of tool 150, e.g., anywhere along proximal portion 156, mid-portion 158, and/or distal portion 160 to apply a downward force as generally indicated by arrow 178 on IMD 100 to force puncturing tips of fixation members 110 through a tissue layer and thereby secure IMD 100 at the implant site. A slight tilt upward of tool 150 and/or withdrawing tool 150 in the proximal direction back out of the pocket and the incision will release IMD 100 from recess 165, leaving IMD 100 securely anchored at the implant site by fixation members 110.

Figure 8:
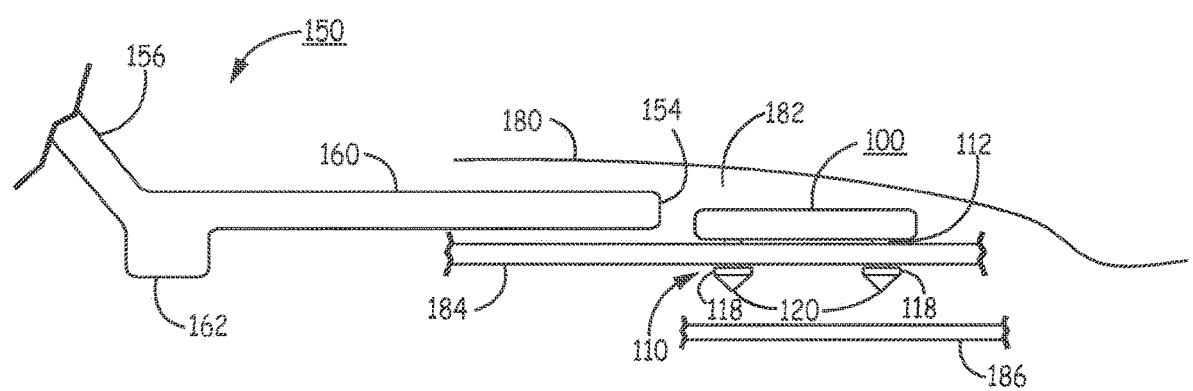
FIG. 8 is a side plan view of the implantation tool and the IMD shown in FIG. 6 after being deploying to desired implant site.

FIG. 8 is a side plan view of the implantation tool 150 and IMD 100 shown in FIG. 6 after deploying IMD 100 to desired implant site. Fixation members 110 have been advanced through a tissue layer 184, such as a deep fascia tissue layer extending over a targeted nerve 186, which may be the tibial nerve. Tool 150 has been advanced via a minimally-sized incision under a tissue layer 180 to form a tissue pocket 182. Downward pressure applied to tool 150 forces puncturing tips 120 through layer 184 such that flanges 118 of fixation members 110 are positioned on an opposite side of tissue layer 184 from IMD 100. Posts 112 extend through the tissue layer, and the length of posts 112 may be selected to correspond to a thickness of layer 184 or a desired depth within layer 184 to deploy flanges 118.

When functional as electrodes, fixation members 110 are now positioned in close proximity to nerve 186 for delivering an electrical stimulation therapy. When electrodes are incorporated along the housing of IMD 100, they are held stably against layer 184 for stimulating nerve 186 from above, i.e. superior to, the tissue layer 184, delivering electrical energy through layer 184. For example, housing-based electrodes may be used to stimulate the tibial nerve through a deep fascia tissue layer. Tool 150 is withdrawn proximally (in the direction of proximal end 152 of tool 150, not visible in the view of FIG. 8), leaving IMD 100 stably anchored at the implant site. Over time, puncturing tips 120 may dissolve or absorb leaving only flanges 118 extending through layer 184.

While tool 150 is shown and described for use in implanting IMD 100 with fixation members 120, tool 150 may be adapted for use with an IMD mounted within the fixation shroud 200 shown in FIG. 5. Retaining sleeve 170 would be appropriately modified to include grooves mating with fixation members 210 such that the sleeve 170 retains the IMD (held within shroud 200) within a recess 165 of tool 150. When retaining sleeve 170 is withdrawn proximally from tool 150, downward pressure applied to tool 150 forces fixation members 210 into a tissue layer to stably anchor shroud 200 carrying the IMD at the implant site. Tool 150 is withdrawn leaving shroud 200 and the IMD secured within the shroud at the implant site. Shroud 200 or portions thereof may dissolve or absorb over time. Shroud 200 may completely absorb over time leaving only the IMD at the implant site.

Figure 9:
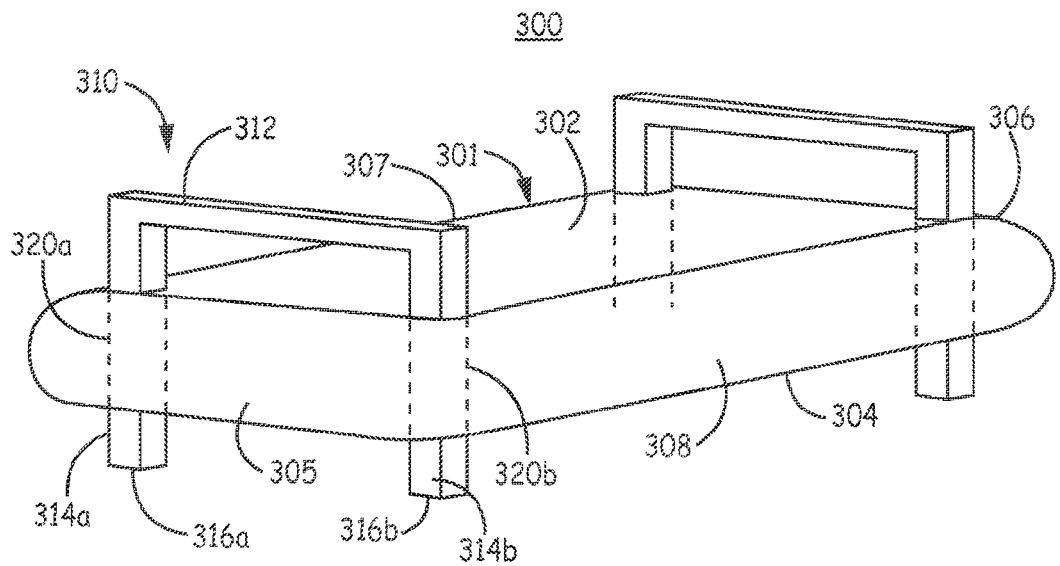
FIG. 9 is a perspective view of an exemplary IMD having active fixation members.

FIG. 9 is a perspective view of an IMD 300 having active housing fixation members 310. IMD housing 301 includes a top face 302 and a bottom face 304 separated by opposing pairs of side walls 305, 306 and 307, 308. Housing 301 includes one or more pairs of lumens 320a, 320b, as indicated by dash line, extending from top surface 302 to bottom surface 304. In some embodiments, housing 301 includes a polymer enclosure, an overmold portion, or a separate cavity that is external to a sealed cavity within housing 301, enclosing IMD circuitry. Lumens 320a, 320b may therefore be positioned through a housing portion that is exterior to a sealed housing cavity or sealed circuitry and does not compromise the hermeticity or fluid resistance of sealed circuitry or a sealed cavity formed to enclose and protect circuitry from corrosion.

One or more fixation members 310 each extend through a pair of lumens 320a and 320b. Fixation member 310 is a substantially "U" shaped, "staple-like" member, having a cross beam 312 and two descending legs 314a and 314b, extending from first and second ends of cross beam 312 through respective housing lumens 320a and 320b. In the embodiment shown, IMD 300 includes two fixation members 310 extending through lumens positioned adjacent opposing end side walls 305 and 306 of housing 301. The arrangement of fixation members 310 and lumens 320 shown in FIG. 9 is illustrative and it is understood that any number of fixation members may be provided extending through lumens positioned at desired anchoring locations along housing 301. In some embodiments, a fixation member 314 is provided at a single end of IMD 300 corresponding to a location of electrodes, in particular a location of a stimulating cathode electrode, positioned along IMD housing bottom surface 304.

Legs 314a and 314b terminate at free ends 316a and 316b, collectively 316. Free ends 316 are shown as blunt ends in FIG. 9 but may alternatively be pointed, rounded or include a dissolvable or absorbable puncturing tip as described above. Free ends 316 may include features to aid in fixation of legs 314, such as barbs, hooks or tines. Free ends 316 may initially be retained within lumens 314a, 314b and be advanced out of the lumens 320, away from bottom face 304 during an implant procedure.

Figure 10:
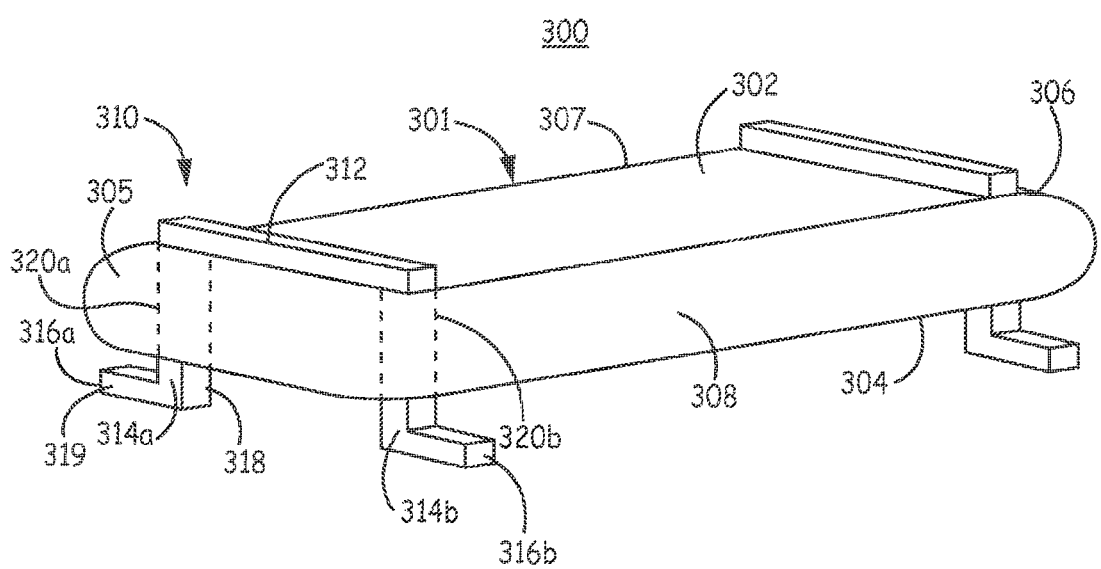
FIG. 10 is a perspective view of the IMD shown in FIG. 9 after deploying fixation members.

FIG. 10 is a perspective view of the IMD 300 shown in FIG. 9 after deploying fixation members 310. Fixation member legs 314a, 314b have a normally flared position as shown in FIG. 10 and are retained in a straight position when confined within lumens 320. During an implantation procedure, pressure is applied to cross beam 312, by hand or using an implant tool, to advance fixation members 310 through lumens 320. Legs 314 extend out from lumens 320 and, no longer being confined within the lumens 320, regain the normally flared position.

In the normally flared position, legs 314 include a descending portion 318 intersecting with a lateral portion 319. When free end 316 is advanced through a tissue layer, lateral portion 319 bends or curves into the flared position. In the flared position, the fixation member legs 314 resist movement up out of the tissue layer, i.e. in a z-direction, thereby urging and anchoring IMD housing bottom face 304 against the tissue layer. The lateral portion 319 may capture a tissue layer between lateral portion 319 and bottom face 304. Descending portions 318 of legs 314a and 314b resist motion of the IMD 300 in the x- and y-directions. In this way, IMD 300 is stably anchored at a desired implant location.

The fixation members 310 are formed such that legs 314a and 314b have a normally flared position, extending laterally outward. For example, legs 314 may bend or curve such that lateral portions 319 approach a plane approximately parallel to cross beam 312. Lateral portions 319 may extend in any direction and are shown to extend in opposite directions, parallel to end side walls 305 and 306, outward from lateral side walls 307 and 308. In other embodiments, lateral portion 319 may extend in other directions, but generally approach a plane that is parallel to bottom face 304 to resist movement in the z-axis. Legs 314 may bend to an approximately 90 degree angle between descending portion 318 and lateral portion 319 such that lateral portion 319 is approximately parallel to bottom face 304. In other embodiments, legs 314 may bend at an angle that is less than or greater than 90 degrees, for example an angle between approximately 45 degrees and 135 degrees.

Fixation member 310 may be formed from nitinol or other superelastic and/or shape memory material. As described above, fixation member 310 is configured to assume a normally flared position, which may occur upon being released from lumens 320 and/or upon reaching body temperature. Fixation member 310 may be formed as a single component. In some embodiments, legs 314 or at least a portion thereof are made from a superelastic or shape memory material and coupled to cross beam 312 which may be formed from another material. Legs 314 or at least a portion thereof may function as electrodes for delivering an electrical stimulation therapy in some embodiments. An extendable conductive interconnect, such as a serpentine interconnect, or other conductive interconnect having excess length or strain relief may electrically couple legs 314 to circuitry enclosed in IMD housing 301. Alternatively a spring contact or other protruding contact formed along lumens 314 may provide electrical connection between legs 314 and IMD internal circuitry to enable legs 314 to function as electrodes.

Figure 11:
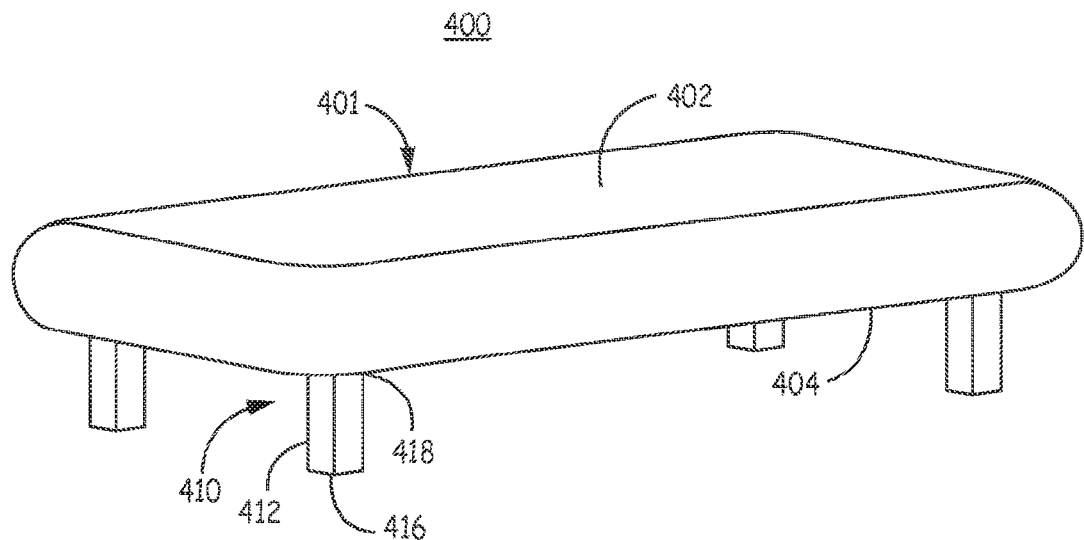
FIG. 11 is a perspective view of an exemplary IMD including shape memory fixation members according to an alternative embodiment.

FIG. 11 is a perspective view of an IMD 400 including shape memory fixation members 410 according to an alternative embodiment. IMD housing 401 includes a top face 402 and bottom face 404. One or more housing fixation members 410 extend from bottom face 404 of housing 401. Fixation member 410 includes a post 412 extending between a proximal end 418 coupled to bottom face 404 to a distal free end 416. End 416 is shown as a blunt end but may be a sharpened or rounded tip or include a dissolvable or absorbable puncturing tip as described previously.

Figure 12:
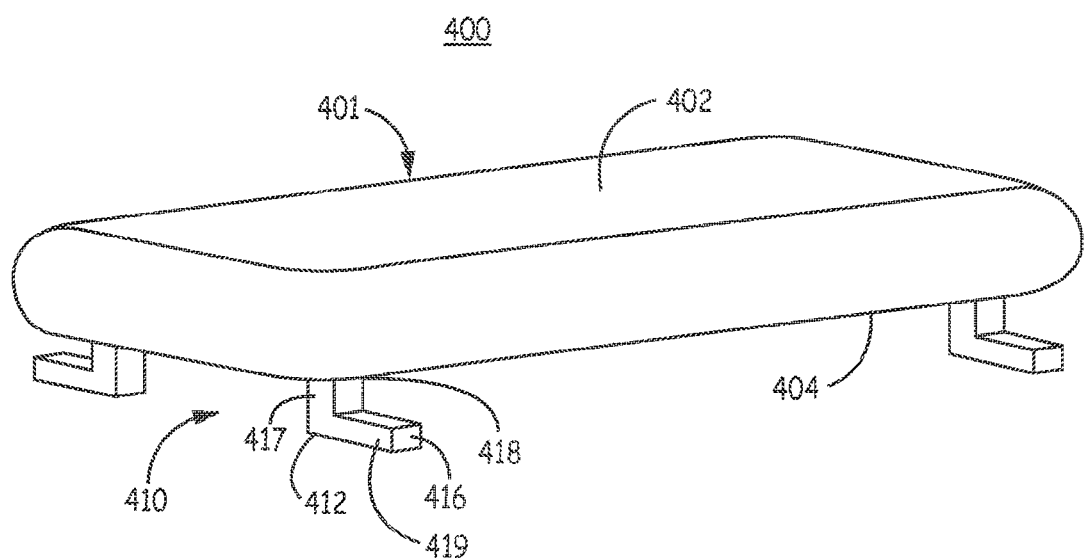
FIG. 12 is a perspective view of the IMD of FIG. 11 with the fixation members in a deployed position.

FIG. 12 is a perspective view of IMD 400 of FIG. 11 with the fixation members 410 in a deployed position. Fixation members 410 include a shape memory material, such as nitinol, such that after IMD 400 is implanted and fixation member free end 416 is advanced through a tissue layer, such as deep fascia, the fixation members 410 bend to a normally flared position upon reaching body temperature.

The normally flared position may correspond to the position shown in FIG. 12 and generally described above in conjunction with FIG. 10, though other positions may be taken which effectively secure fixation member 410 under or within a tissue layer to resist movement of IMD 400. For example, post 412 will bend such that a descending portion 417 bends or curves into a lateral portion 419 that approaches a plane parallel to bottom face 404. Free distal end 416 may extend inwardly under bottom face 404 or outwardly away at any desired angle. Free distal end 416 may include one or more protruding features, such as a barb, hook or tine, for aiding in fixation of post 412. Any protruding features may also be formed of the shape memory material such that initially a protruding fixation feature extends alongside the post 412 and becomes flared or outwardly extending upon reaching body temperature.

A portion or all of post 412 may be an electrically active surface for functioning as an electrode. Post 412 may be electrically coupled to internal IMD circuitry housed in housing 401 via a feedthrough through bottom face 404 or an electrical interconnect within housing 401.

Figure 13:
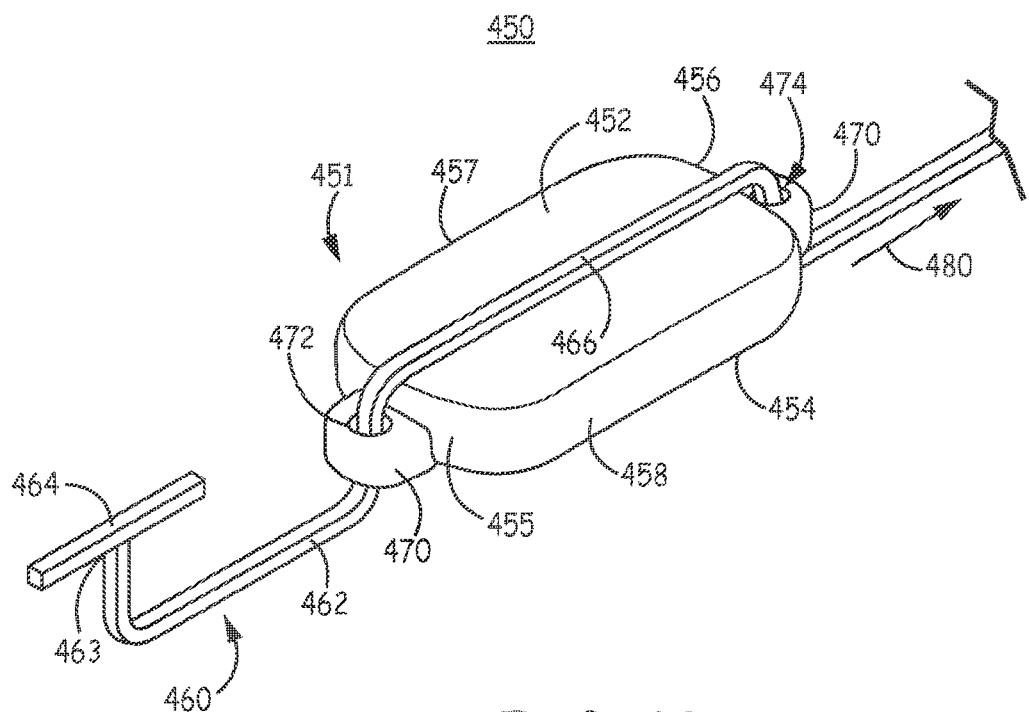
FIG. 13 is an exemplary IMD including a fixation member according to an alternative embodiment.

FIG. 13 is an IMD 450 including a fixation member 460 according to an alternative embodiment. IMD 450 includes a housing 451 having top face 452 and bottom face 454 separated by end side walls 455 and 456 and lateral side walls 457 and 458. Housing 451 includes protruding tabs 470, shown extending from end side walls 455 and 456. The positions of tabs 470 are illustrative and may vary between embodiments.

Tabs 470 include an inner surface 472 defining an aperture 474 through which a housing fixation member 460 can be threaded. Fixation member 460 includes a flexible elongate body 462, which may be a wire or suture, having a fixating structure 464 at elongate body distal end 463. The elongate body 462 is threaded through apertures 474 of tabs 470 such that a portion 466 of body 462 extends along top face 452. A proximal end (not shown in FIG. 13) of elongate body 462 may be threaded through a needle in some embodiments.

Fixating structure 464 may be in the form of a "T-bar" that intersects approximately perpendicularly with body 462 as shown in FIG. 13, but may alternatively be a barb, tine, hook, helix or other fixating structure. In some embodiments, T-bar structure 464 may further include barbs or tines extending from the T-bar. During an implant procedure, as will be further described below, the fixating structure 464 is advanced through a tissue layer, for example by loading fixating structure 464 into a lumen of a hypodermic-like needle and puncturing the needle through a tissue layer.

When the needle is withdrawn, the fixating structure 464 will resist being pulled back through the tissue layer. Elongate body 462 can be pulled proximally in the direction indicated by arrow 480 to remove any slack or excess length of elongate body 462 between tab 470 at end side wall 455 and fixating structure 464. In this way, tissue is captured between fixating structure 464 and tab 470 at end side wall 455. A proximal end of elongate body 462, which can be threaded through an eye of a surgical needle, may be anchored in tissue near tab 470 using a suture stitch that allows elongate body 462 to be pulled in the proximal direction 480, tightened across top surface 452, and subsequently knotted or clipped to hold bottom face 454 securely against the tissue layer by elongate body 462. Fixation member 460 is anchored in place by fixating structure 464 at end side wall 455 and by a knotted or clipped suture stitch at end side wall 456, thereby anchoring IMD 450 in place.

Figure 14:
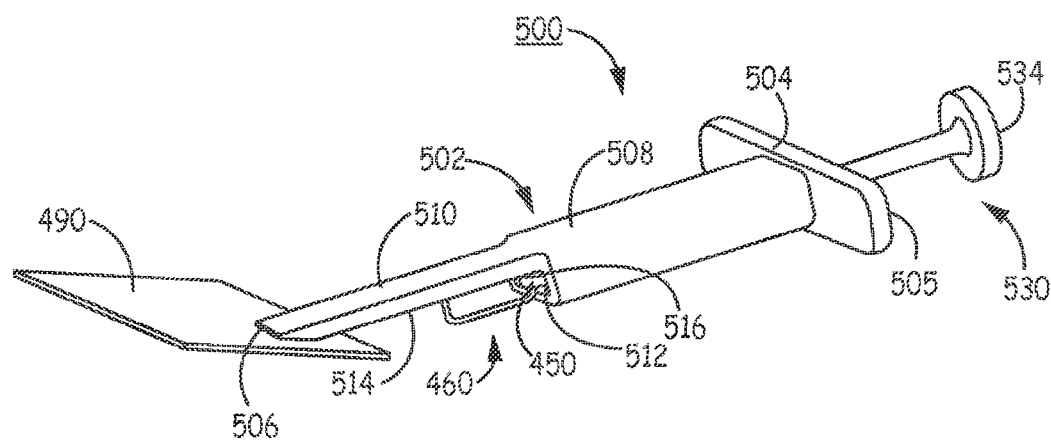
FIG. 14 is a perspective view of an exemplary implantation tool for use in implanting the IMD shown in FIG. 13.

FIG. 14 is a perspective view of an implantation tool 500 for use in implanting IMD 450 shown in FIG. 13. Implantation tool 500 includes a syringe body 502 and a plunger 530. Syringe body 502 extends from a proximal end 504 to a distal end 506. Distal end 506 may be a smooth or atraumatic end for applying to a tissue layer 490. Alternatively, distal end 506 may be a sharpened dissecting edge to cut through skin or a blunt dissecting edge for forming the IMD pocket. Proximal end 504 may include a stop surface 505 to interface with a plunger stop surface 534.

Syringe body 502 includes a distal needle guiding portion 510 extending proximally from the distal end 506 and a proximal IMD guiding portion 508 extending between proximal end 504 and distal needle guiding portion 510. The needle guiding portion 510 may include an open side (not seen in the view of FIG. 14), and an inner surface defining a lumen 514 through which fixation member 460 is guided distally via a hypodermic like needle portion of plunger 530 (not seen in FIG. 14).

IMD guiding portion 508 includes an inner surface 512 defining a lumen large enough to retain IMD 450. As plunger 530 is advanced into syringe body 502, the fixation structure 464 of fixation member 460 will be inserted through tissue layer 490. As the plunger 530 is advanced, IMD 450 will be concomitantly ejected from syringe body 508 through opening 516 defined by inner surface 512 and securely anchored against tissue layer 490 as will be discussed in greater detail below.

It is noted that the fixation member 460 is shown to have a diameter that is exaggerated relative to the IMD 450 size for the sake of illustration. The diameter of a wire or suture forming elongate body 462 may be much smaller relative to the IMD 450. Furthermore, while it is shown to generally have a square cross-section in the artists' rendering, the elongate body 462 and T-bar structure may have different cross-sectional shapes, which may include generally round or flattened cross-sections.

Figure 15:
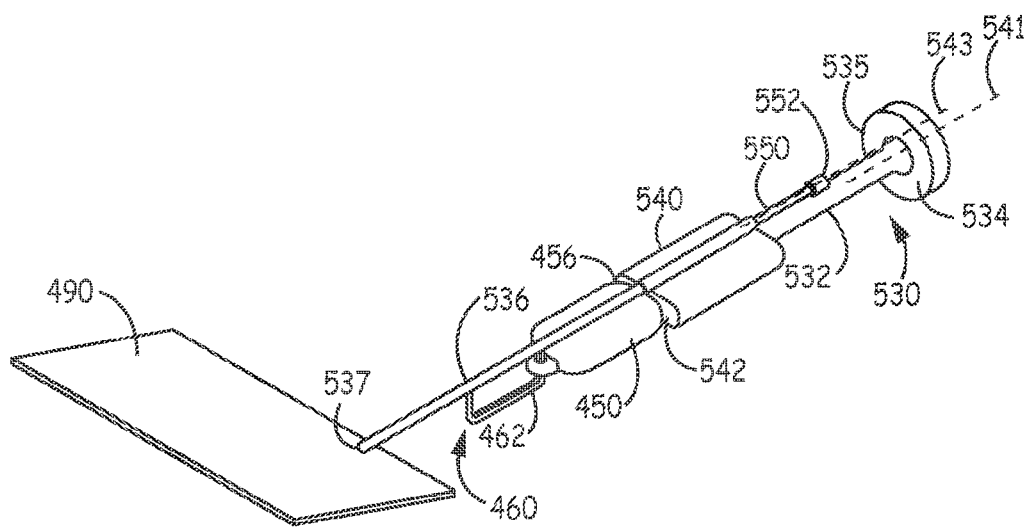
FIG. 15 is a perspective view of an exemplary IMD and plunger of the implantation tool shown in FIG. 14.

FIG. 15 is a perspective view of IMD 450 and plunger 530 of the implantation tool 500 shown in FIG. 14. Plunger 530 extends between a proximal end 535 and a distal end 537 and includes a proximal shaft 532, a mid-portion 540, and a distal hollow needle portion 536. Proximal end 535 includes a stopping interface 534 that enables a user to advance plunger 530 a controlled distance into syringe body 502 shown in FIG. 14. Distal end 537 is a sharpened tip of a distal hollow needle portion 536 of plunger 530. Fixating structure 464 is loaded in hollow needle portion 536.

Distal hollow needle portion 536 extends along top surface of IMD 450 and along at least a portion of a mid-portion 540 of plunger 530. Mid-portion 530 includes a distal face 542 that interfaces with IMD end side wall 456 within IMD guiding portion 508 of syringe body 502. Distal face 542 may be contoured or include an open groove to receive tab 470 positioned along end side wall 456. Elongate body 462 of fixation member 460 may extend alongside needle portion 546 over the IMD or within a slot or lumen of needle portion 546. When plunger 530 is advanced, distal face 542 of plunger mid-portion 540 advances IMD 450 out a distal opening 516 (FIG. 14) of IMD guiding portion 508 of syringe body.

Distal hollow needle 536 has a longitudinal central axis 543 offset from a longitudinal central axis 541 of proximal shaft 532. A second, smaller plunger 550 extends into a lumen of distal hollow needle portion 536. Second plunger 550 is advanced into hollow needle portion 536 when the proximal end 535 of plunger 530 is depressed. Stopping interface 534 of plunger 530 presses against second plunger head 552, thereby advancing second plunger 550 into hollow needle portion 536.

Figure 16:
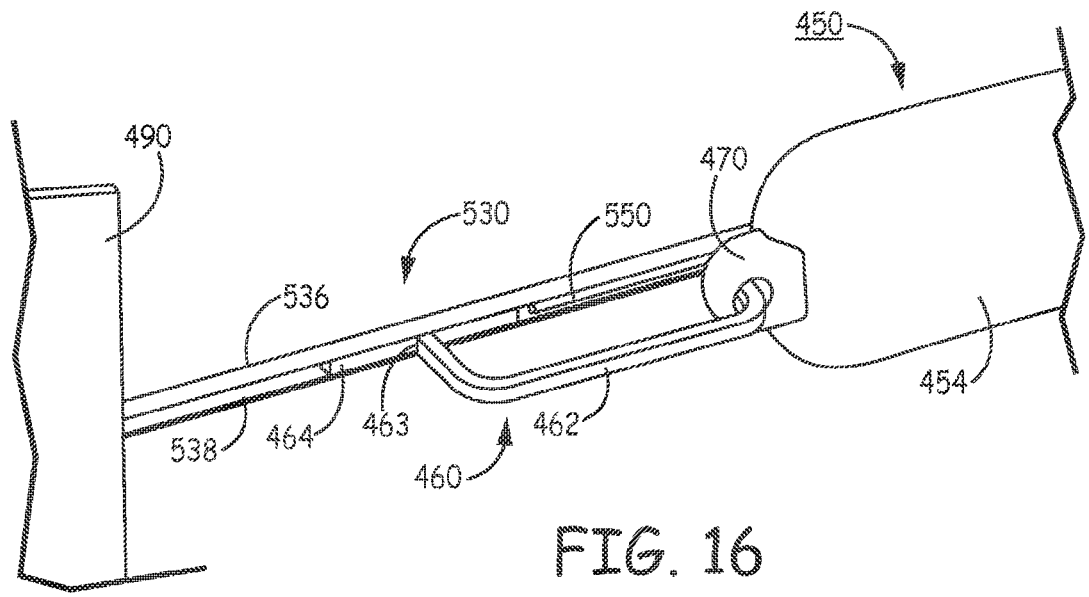
FIG. 16 is a close-up bottom perspective view of the plunger shown in FIG. 15.
Figure 17:
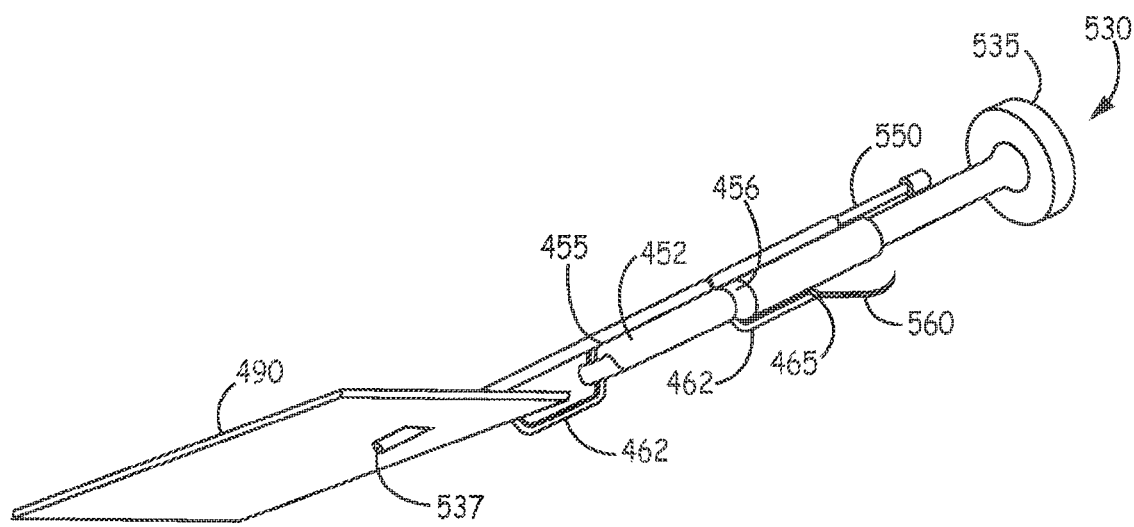
FIG. 17 is perspective view of the plunger of FIG. 15 from a different angle.

FIG. 16 is a close-up bottom perspective view of plunger 530, and FIG. 17 is perspective view of plunger 530 from a different angle. Distal needle portion 536 includes an open side 538 that receives fixating structure 464 and enables fixating structure 464 coupled to the distal end 463 of fixation member body 462 to freely advance along the distal needle portion 536 as the second plunger 550 is advanced through needle portion 536 when the proximal end 535 of plunger 500 is depressed into syringe body 502 (FIG. 14).

Distal sharpened tip 537 is punctured through a tissue layer 490. Then, in one step of depressing plunger proximal end 535, fixating structure 464 is deployed through the tissue layer 490, and IMD 450 is delivered concomitantly from the syringe body and positioned over the tissue layer 490. A proximal end 465 of elongate body 462 may be pre-threaded on a surgical needle 560. Fixation member 460 may be provided with an elongate body 462 having a greater length than shown, such that excess length is available for suturing using needle 560. After removing implantation tool 500, the needle 560 can be used to anchor end side wall 456 by placing a suture in close proximity to tab 470 through tissue layer 490, then tightening elongate body 462 over top face 452 and securing elongate body 462 with a knot or using a tined elongate body 462 that does not require knotting to be anchored in place.

Figure 18:
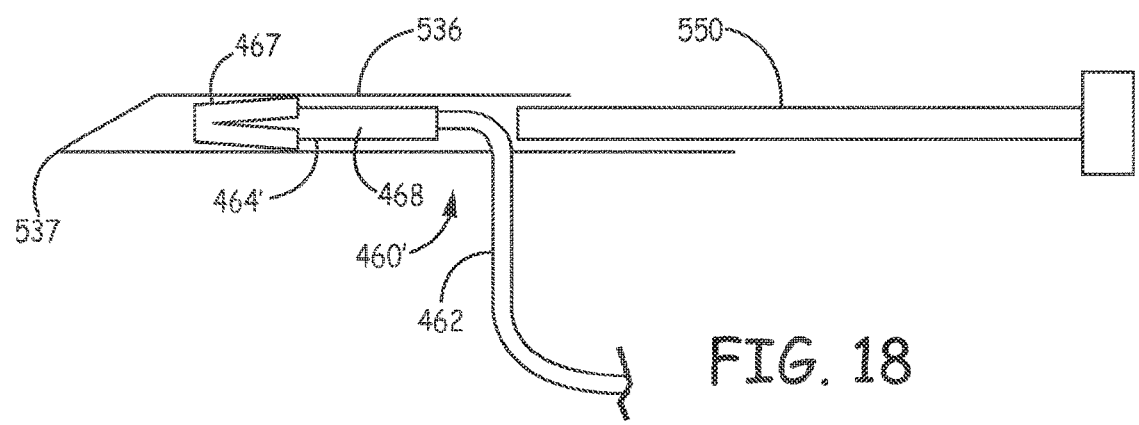
FIG. 18 is a side view of an exemplary fixation structure loaded in the hollow needle of the implant tool shown in FIG. 14 according to an alternative embodiment.

FIG. 18 is a side view of fixating structure 464' loaded in the hollow needle 536 of the implant tool 500 shown in FIG. 14 according to an alternative embodiment. In this embodiment, fixating structure 464' includes flexible tines 467 that can collapse against a shaft portion 468 of fixating structure 464'. The tines 467 are held against shaft portion 468 when confined within a lumen of hollow needle 536. Shaft portion 468 is shown coaxially aligned with respect to a longitudinal central axis of elongated body 462 and coupled to the elongated body 462 of fixation member 460'.

Figure 19:
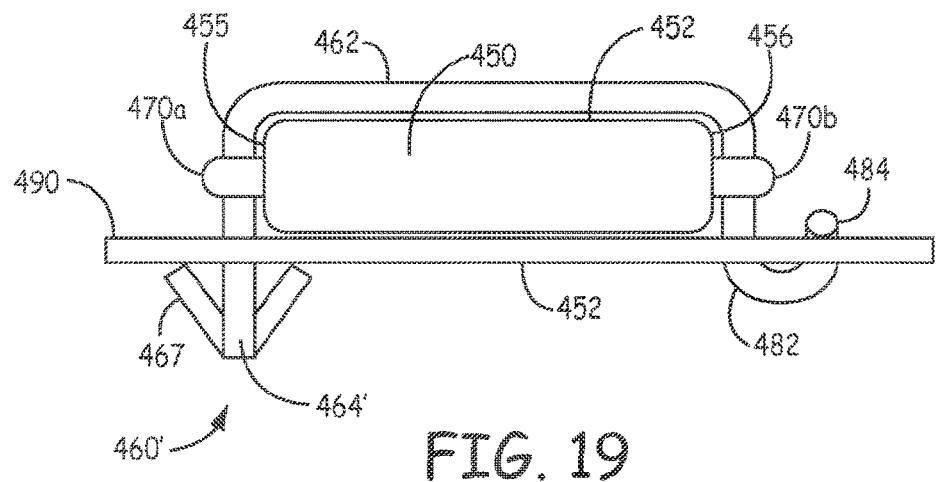
FIG. 19 is a side view of an exemplary IMD fixed at a desired implant location using the fixation structure shown in FIG. 18.

FIG. 19 is a side view of an IMD 450 fixed at a desired implant location using the fixating structure 464' shown in FIG. 18. With continued reference to FIG. 18, distal sharpened tip 537 is advanced through tissue layer 490. When the second needle plunger 550 is advanced distally in hollow needle 536, fixating structure 464' is advanced out a distal opening of needle 536. Needle 536 is withdrawn allowing tines 467 to expand to a normally flared position as shown in FIG. 19. Tines 467 resist withdrawal of fixation member 460' through the tissue layer 490. Elongate body 462 extends through tabs 470a and 470b on respective end side walls 455 and 456 and across top face 452.

Elongate body 462 is guided through tissue layer 490 using a surgical needle to secure IMD 450 in the vicinity of end side wall 456 with a suture 482 through tissue layer 490. A knot or clip 484 on elongate body 462, on the outer surface of tissue layer 490, secures elongate body 462 in a taut position to anchor IMD 450 against tissue layer 490 at the implant site.

Figure 20:
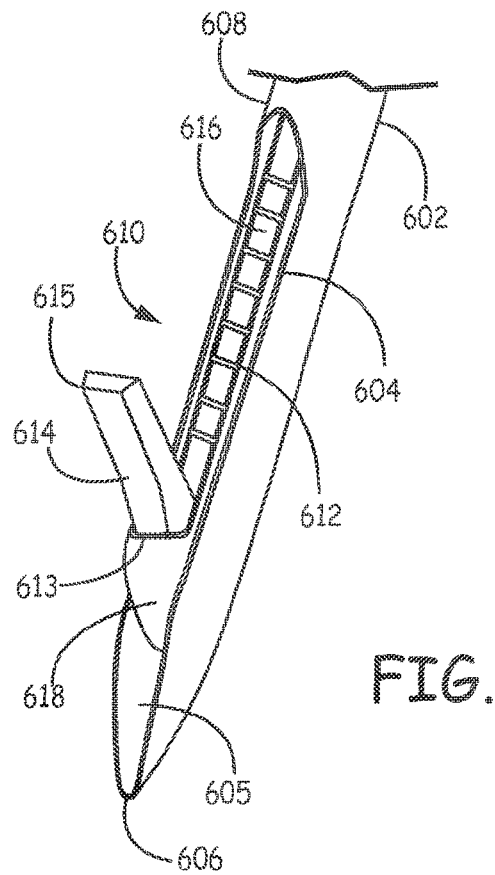
FIG. 20 is a close-up perspective view of an alternative exemplary embodiment of a fixation member loaded in a hollow needle.

FIG. 20 is a close-up perspective view of an alternative embodiment of a fixation member 610 loaded in a hollow needle 602. Fixation member 610 includes an elongate body 612 having a serrated surface 616. Fixation member 610 further includes a flange 614 having a first end 613 attached at or near a distal end 618 of body 612. A second, free end 615 of flange 614 extends outward from a longitudinal center axis of body 612.

Hollow needle 602 has a sharpened distal tip 606 for penetrating a tissue layer for deploying flange 614 in or beneath a tissue layer at a target implant site. Hollow needle 602 may include an open side or slot 604 that enables flange 614 to project outward when fixation member 610 is loaded in needle 602. In other embodiments, flange 614 may be collapsed against elongate body 612 when confined within a closed lumen of needle 602.

In one embodiment, fixation member 610 may be confined within a proximal closed lumen portion 608 until distal tip 602 is advanced a desired depth within or through a tissue layer. Fixation member 610 may then be advanced out of a distal opening 605. Open side 604 of the distal portion of needle 602 allows flange 614 to project outward but not until flange 614 is beneath or within the tissue layer. When needle 602 is withdrawn, flange 614 resists withdrawal of the fixation member 610.

Figure 21:
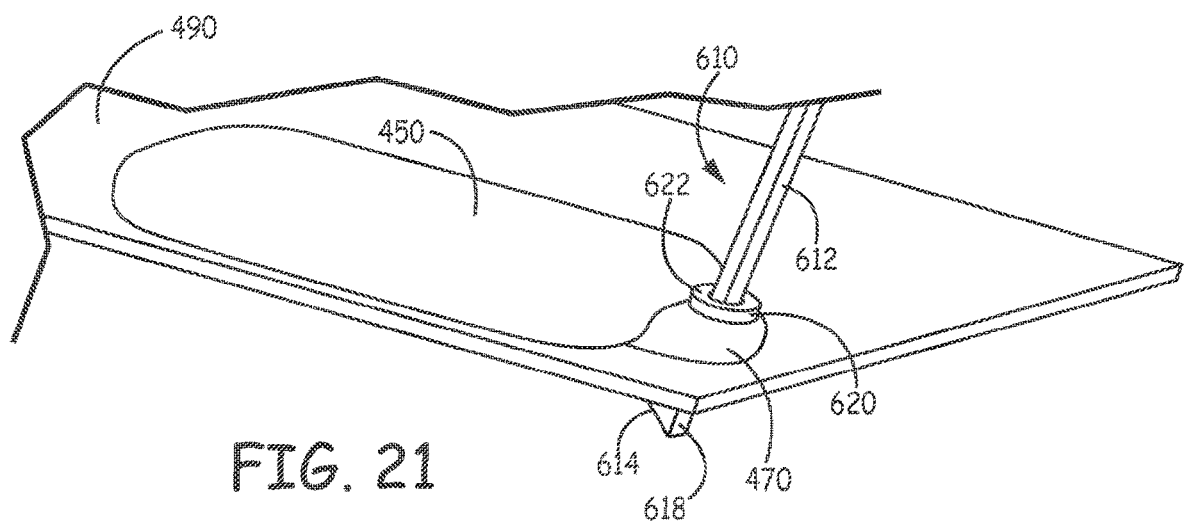
FIG. 21 is a perspective view of the fixation member shown in FIG. 20 deployed for anchoring an IMD against a tissue layer.

FIG. 21 is a perspective view of fixation member 610 shown in FIG. 20 deployed for anchoring an IMD 450 against a tissue layer 490. IMD 450 includes a tab 470 having an inner surface defining an opening as shown and described previously. In FIG. 21, IMD 450 is shown having only one tab 470, however, IMD 450 may include multiple tabs 470 for use in anchoring IMD 450 at a desired implant site. The location of tab 470 on IMD 450 is illustrative and it is recognized that one or more tabs may be positioned along any side wall of IMD 450.

Needle 602 is advanced through the opening in tab 470 to deploy flange 614 beneath tissue layer 490 as generally described in conjunction with FIG. 20. A ratcheting collet 620 is then advanced down elongate body 612. Ratcheting collet 620 includes an interlocking inner surface 622 that interlocks with a serration on elongate body serrated surface 616 (shown in FIG. 20).

Ratcheting collet 620 freely moves distally along elongate body 612 (toward distal end 618) but by interlocking with serrated surface 616, ratcheting collet 620 cannot be moved proximally along elongate body 612. Accordingly, ratcheting collet 622 is advanced along elongate member 612 until tab 470 is firmly held against tissue layer 490 and tissue layer 490 is securely captured between flange 614 and tab 470. Elongate body 612 may then be trimmed off just above ratcheting collet 620. In some embodiments, the serrated surface 616 may be terminated a distance from distal end 618 to prevent over-tightening of the fixation member 610 potentially causing excessive squeezing of tissue layer 490.

Figure 22:
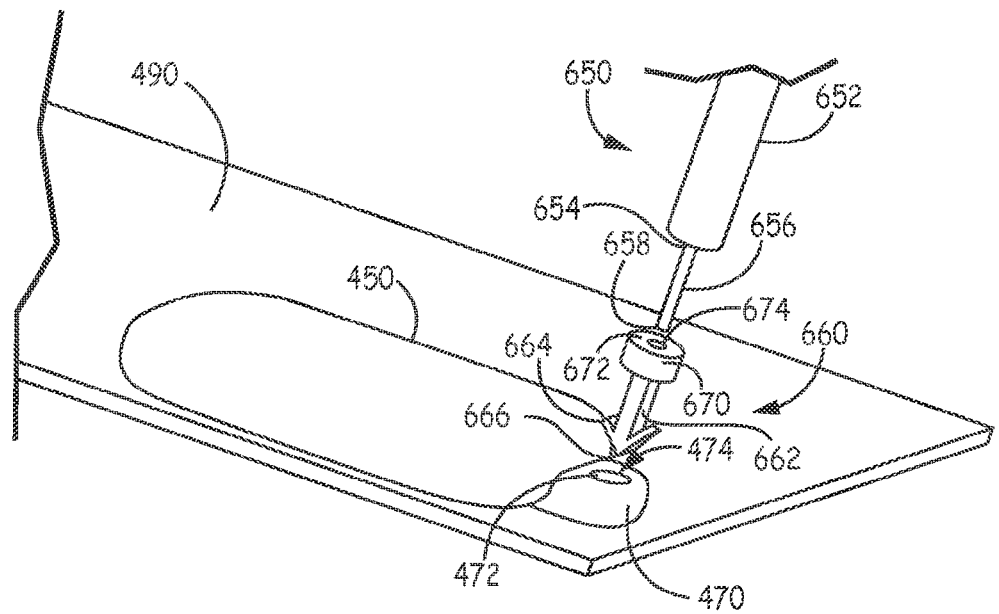
FIG. 22 is a perspective view of an alternative exemplary embodiment of an IMD fixation member.

FIG. 22 is a perspective view of an alternative embodiment of an IMD fixation member 660. Fixation member 660 includes a shaft 662 and head 670 having a diameter greater than shaft 662 and greater than the aperture 474 defined by inner surface 472 of IMD tab 470. Shaft 662 includes distal flanges or tines 664 that protrude radially outward from shaft 662. Tines 664 may be inwardly flexible. Tines 664 are attached to shaft 662 at or near a shaft distal end 666. Shaft distal end 666 may be pointed to facilitate advancement through tissue layer 490.

Fixation member 660 is advanced through aperture 474 of tab 470 and through tissue layer 490 using an implant tool 650. Tool 650 includes a handle portion 652 and a tool shaft 656 having a distal end 658. Handle portion 652 includes a distal face 654 for interfacing with a top surface 672 of head 670 when tool shaft 656 is advanced into a central lumen 674 of fixation member 660. Central lumen 674 may have a closed end such that distal end 658 meets with a closed end of lumen 674 (not shown in the perspective view of FIG. 22) to apply force to insert fixation member 662 through tissue layer 490.

Fixation member 660 is pushed through tab 470 until head 670 meets tab 470. Accordingly, a length of fixation member shaft 662 can be selected to reach a desired depth of deploying tines 664 beneath or within tissue layer 490.

Figure 23:
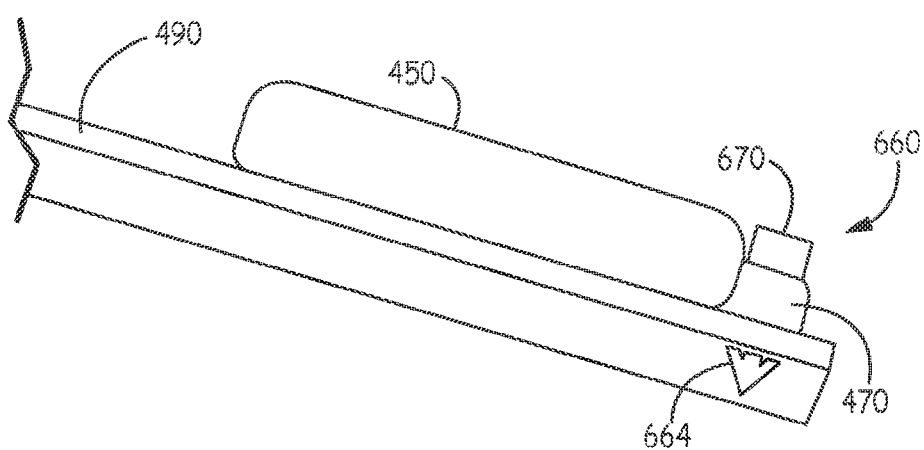
FIG. 23 is a perspective view of an exemplary fixation member anchoring an IMD against a tissue layer.

FIG. 23 is a perspective view of housing fixation member 660 anchoring IMD 450 against tissue layer 490. Tines 664 have been deployed beneath tissue layer 490 to resist movement of IMD 450 in a z-direction and migration of IMD 450 along tissue layer 490. A second fixation member 660 may be employed (through a second tab) to resist movement of IMD 450 in all directions. Tab 470 and tissue layer 490 are captured between fixation member head 670 and tines 664. Fixation member 660 may be wholly or partially formed from a polymer such as a polyurethane, polysulfone, epoxy, silicone or other biostable polymer material. Alternatively fixation member 660 or portions thereof may be formed of a bioabsorbable material that will be absorbed over time, providing early fixation after implant, until tissue encapsulation takes place and allowing easier explantation of IMD 450 at a later time. In other embodiments, fixation member 660 or portions thereof may be formed of a metal, such as but not limited to titanium, stainless steel, or platinum or alloys thereof.

Figure 24:
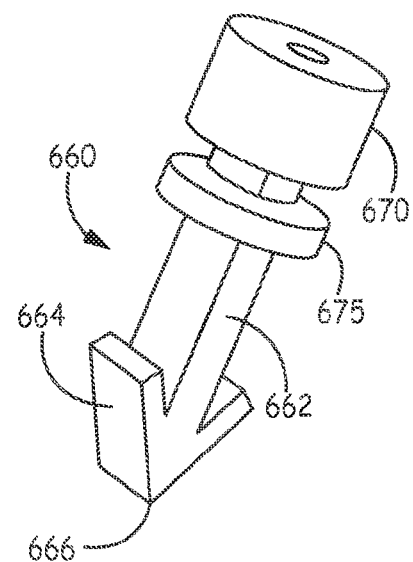
FIG. 24 is a perspective view of the fixation member shown in FIG. 22 including a compliant grommet.

FIG. 24 is a perspective view of the fixation member 660 shown in FIG. 22 including a compliant grommet 675. In some embodiments, fixation member 660 may be formed of an elastomer such as polyurethane 80A or silicone. The fixation member 660 has a durometer sufficient to be forced through the tissue layer 490, which may vary depending on the properties of tissue layer 490, and elasticity that enables it to return to an original dimension. The length of shaft 662 may be selected to provide a snug but compliant "fit" around tissue layer 490 and tab 470.

In other embodiments a fixation member 660 may be fabricated from a rigid material. In these embodiments, a compliant grommet 675 circumscribing shaft 662 may be included to provide the desired compliance of fixation member 660 when tissue layer 490 is sandwiched between tines 664 and head 670.

Figure 25:
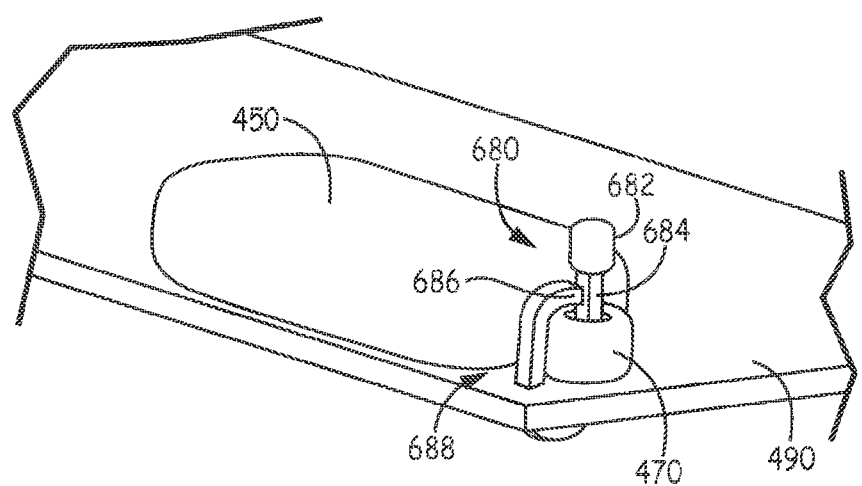
FIG. 25 is a perspective view of an alternative exemplary fixation member including a "U" shaped clip.

FIG. 25 is a perspective view of an alternative fixation member 680 including a "U" shaped clip 688. Fixation member 680 includes a proximal head 682 and a shaft 684 extending from the proximal head 682 to a distal end 686. Fixation member shaft 684 is fabricated from nitinol or another shape memory or super elastic material having a normally curved position in the "U" shape as shown in FIG. 25. When confined within the lumen of an implantation tool, such as a hollow needle, fixation member shaft 684 is retained in a straight position. The needle is advanced through tab 470 and tissue layer 490 to position distal end 686 under tissue layer 490. As the needle is withdrawn, shaft 684 springs back into the normal, pre-formed "U" shaped position. Distal end 686 will pierce upward through tissue layer 490 to meet shaft 684 along a proximal portion of shaft 684 as shown. Distal end 686 may be provided as a sharpened tip to facilitate piercing back through tissue 490. The resulting "U" shaped clip 688 holds tab 470 in place thereby anchoring a position of IMD 450 over tissue layer 490.

In an alternative embodiment, the shaft 684 is hollow and an implantation tool includes a wire or shaft that extends through the fixation member shaft, holding it in a straight position until it has been advanced through tab 470 and into a tissue layer. Upon removing the tool from the fixation member shaft, the shaft assumes a deployed, U-shaped position.

Figure 26:
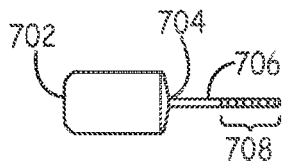
FIG. 26 is a plan view of an exemplary IMD including a housing enclosing internal IMD circuitry and a lead tethered to the housing via an electrically insulated, sealed feedthrough.

In the embodiments described above, the IMDs are generally shown as leadless devices in which electrodes may be incorporated in or along the housing of the IMD. Stimulation of a nerve underlying tissue layer 490 occurs through tissue layer 490 when electrodes are positioned along the IMD housing. In other embodiments, electrodes may be carried by a lead extending away from the IMD. Secure anchoring of the IMD and the lead during a minimally invasive procedure is desired. Techniques and tools are described below for anchoring an IMD and lead system during a minimally invasive procedure. FIGS. 26-28 depict various embodiments of an IMD system for delivering neurostimulation therapy that include electrodes carried by a lead extending away from the IMD housing.

FIG. 26 is a plan view of an IMD 700 including a housing 702 enclosing internal IMD circuitry and a lead 706 tethered to the housing 702 via an electrically insulated, sealed feedthrough 704. The lead 706 is tethered to the IMD 700 in that it is not designed to be disconnected from housing 702. Rather, IMD 700 comes assembled as a single unit including both the housing 702 and associated circuitry tethered in a non-removable manner to lead 706. Lead 706 includes one or more electrodes 708 spaced apart and typically carried near a distal lead end. The electrodes 708 are coupled to internal IMD circuitry via electrical feedthrough 704 and conductors extending through lead 706 between electrodes 708 and feedthrough 704. In one example, lead 706, and other leads coupled to an IMD housing described herein for deployment as a single unit with the IMD, is not more than approximately 5 cm in length. In another example, lead 706 is less than approximately 2 cm in length. In yet another example, lead 706 is approximately 1 cm in length or less.

Figure 27A:
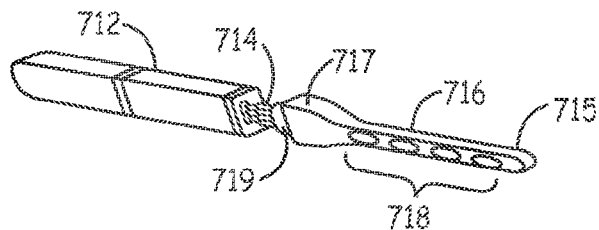
FIG. 27A is a perspective view of an exemplary IMD including a housing and a receptacle for receiving a connector of a lead.
Figure 28:
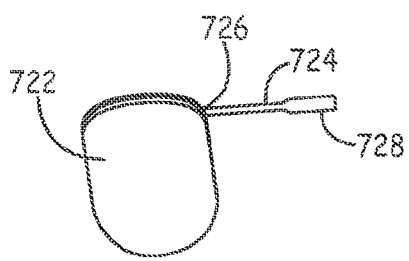

FIG. 27A is a perspective view of an IMD 710 including a housing 712 and a feedthrough receptacle 714 for receiving a connector 719 of a lead 716. One or more electrodes 718 are electrically coupled to circuitry enclosed in IMD housing 712 via connector 719, which is coupled to insulated feedthroughs in receptacle 714. Alternatively, the lead 716 may be bonded to housing 712, e.g. using a braze, weld, locally heated glass seal, or other joining methods such that lead 716 is a non-removable/non-disconnectable lead. The lead 716 includes a proximal connector portion 717 and a flattened distal paddle portion 715 carrying multiple electrodes 718 adapted to be positioned along a targeted nerve, e.g. the tibial nerve, for delivering a neurostimulation therapy. Distal paddle portion 715 may be adapted for positioning and extending superior to, and possibly superficially, to the flexor retinaculum with electrodes 718 selectable for delivering stimulation pulses to the tibial nerve through a deep fascia tissue layer. Alternatively, at least a portion of paddle-shaped portion 715 may be inserted beneath (or deeper than) the retinaculum and/or a deep fascia tissue layer to position electrodes in closer proximity to the tibial nerve. IMD housing 712 and/or lead 716 may be anchored to the deep fascia, or other tissue layer, using any of the fixation methods described above.

Figure 27B:
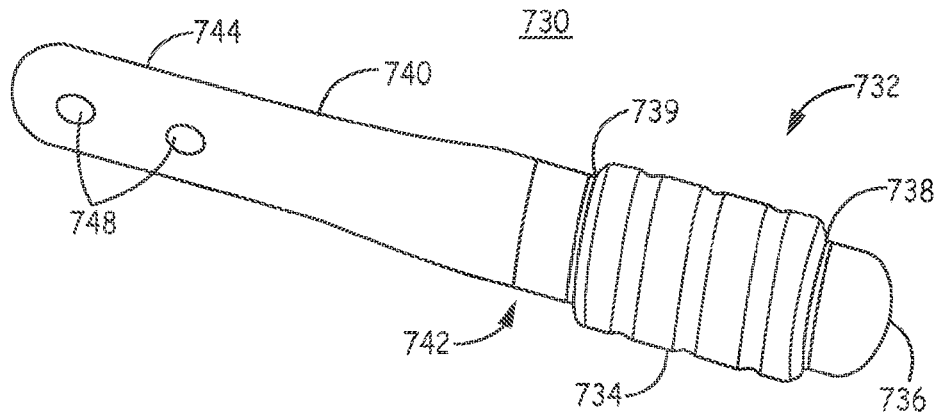
FIG. 27B is a perspective view of an alternative exemplary embodiment of an IMD having a tethered lead.

FIG. 27B is a perspective view of an alternative embodiment of an IMD 730 having a tethered lead 740. IMD 730 includes a sealed housing 732, which may include an end cap 736 bonded or welded to a first housing end 738 and an enclosure 734, which may be an overmold member that seals and protects joints or seams of the housing 732. A proximal end 742 of lead 740 is tethered to housing 732 at a second housing end 739. Lead proximal end 742 may serve as an end cap to seal a cavity enclosed within housing 732. Electrical conductors extending from electrodes 748 extend through lead 740 to proximal end 742 where they may be electrically coupled to IMD circuitry via electrical feedthroughs at housing end 739.

Lead 740 includes a flattened paddle portion 744 carrying electrodes 748. Paddle portion 744 has a thin, flattened cross-section as compared to the semi-circular cross-section of paddle portion 715 of FIG. 27A. A flattened side of lead 740 facilitates positioning of the flattened side against a tissue layer upon deployment from a delivery tool. IMD housing 732 has a generally circular cross-section as compared to a rectangular cross-section of the IMD housing 712 in FIG. 27A. It is contemplated that a lead body shape, i.e. a paddle portion of a lead tethered or connected to an IMD housing, may vary in cross-section between embodiments. The cross-sectional shape of the lead and size and spacing of electrodes carried by the lead may be adapted for a particular anatomical fit at a targeted therapy site. Likewise, the IMD cross-sectional shape and overall size may be adapted for a particular anatomical fit at a targeted implant site.

The housings 712 and 732 shown in FIGS. 27A and 27B and other housings described herein may be adapted to have a variety of polygonal, circular, elliptical or other rounded cross-sectional shapes and profiles to best suit a particular implant site, implantation delivery tool, implantation procedure or other application-specific requirements. For example, an IMD having a semi-circular or semi-elliptical shape or other convex profile may be particularly well-suited for implantation superior to the flexor retinaculum in the region of the medial malleolus for delivering a neurostimulation therapy to the tibial nerve. The anatomical contour in this region includes a concave portion along which a convex portion of the IMD housing, which may be carrying stimulation electrodes, may be positioned to naturally conform to the patient's anatomy in a stable, comfortable and unobtrusive manner.

FIG. 28 is a perspective view of an IMD 720 including a housing 722 tethered to an elongated lead adaptor 724 at an electrically insulated sealed electrical feedthrough 726. Lead adaptor 724 includes a receptacle 728 configured to receive a connector of a lead that is electrically coupled to IMD 720 for delivering neurostimulation pulses via electrodes carried by the lead. Rather than being connected/disconnected at a receptacle formed along a side of or incorporated in the IMD housing 712, the receptacle 728 is extended away from IMD 722 by adaptor 724.

Figure 29A:
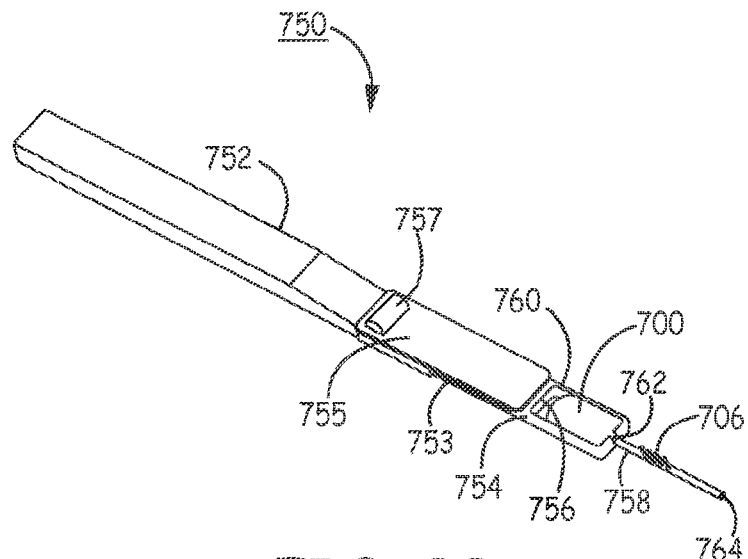
FIGS. 29A and B are perspective views of an exemplary implant tool and the IMD shown in FIG. 26.
Figure 29B:
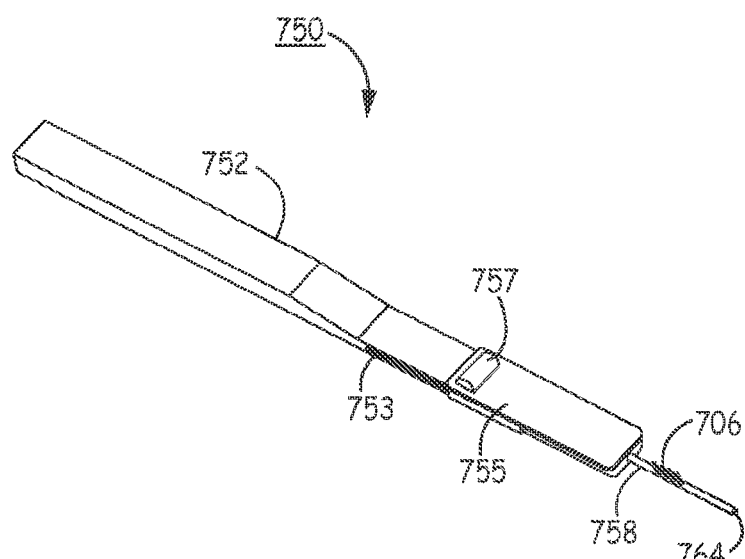

FIG. 29A and FIG. 29B are perspective views of an implant tool 750 shown in open and closed positions, respectively, with IMD 700 shown in FIG. 26 positioned in the tool 750. The tools and techniques described below in conjunction with FIGS. 29-35 refer to the IMD 700 shown in FIG. 26 for illustrative purposes. The embodiments shown in FIGS. 29-35, however, may be adapted for use with any of the embodiments of IMD systems shown in FIGS. 26-28 which include a lead or adaptor extending from the IMD housing that may be removably or non-removably tethered to the IMD to form a single IMD-lead unit. For example, the size and dimensions of cavities or lumens for receiving the IMD and the lead may be adapted as needed to receive different shapes and sizes of IMD-lead units.

Implant tool 750 includes a handle portion 752, a first shaft portion 754 and a second shaft portion 758. First shaft portion 754 is at least partially hollow and extends between handle portion 752 and second shaft portion 758. A side wall 756 of first shaft portion 754 defines an opening or cavity 760 in shaft portion 754 for receiving IMD 700.

Second shaft portion 758 extends from first shaft portion to a distal tool end 764 and is an open-sided, hollow needle defining a cavity for receiving lead 706 tethered to IMD 700. The distal opening 762 of first shaft portion 754 communicates directly with the open-sided lumen second shaft portion 758 so that IMD 700 and lead 760 coupled to IMD 700 can be positioned into tool 750 as a single unit.

Tool 750 may include a removable or movable cover 755, for example a slidable, hinged, or clam shell cover, fitting over at least a portion of one or both of first shaft portion 754 and second shaft portion 706 to enclose or retain IMD 700 and lead 706 after being installed in cavity 760 and the lumen of second shaft portion 758 respectfully. In the example shown, cover 755 is a slidable cover that retains IMD 700 within cavity 760. Cover 755 may glide along ridges 753 formed along lateral sides of first shaft portion to enable an open position as shown in FIG. 29A for insertion and removal of IMD 700 and a closed position as shown in FIG. 29B for removal of IMD 700. Cover 755 may further include a grip 757 or other friction feature that enables a user to apply pressure to slide cover 755 between open and closed positions.

In operation, after IMD 700 and lead 706 are inserted into too 750, cover 755 is moved to a closed position. The tool 750 would be turned over to face the cover 755 down toward a tissue pocket and advanced into an implant site.

Distal tool end 764, which may include a sharpened or tissue penetrating tip, may be inserted through a tissue layer to implant a distal end of lead 706 and one or more electrodes carried by lead 706 along or beneath a tissue layer at a desired implant site. After inserting lead 706 to a desired tissue depth, the cover 755 may be slid open or removed so that IMD 700 and lead 706 can be fully removed from tool 750.

Figure 30:
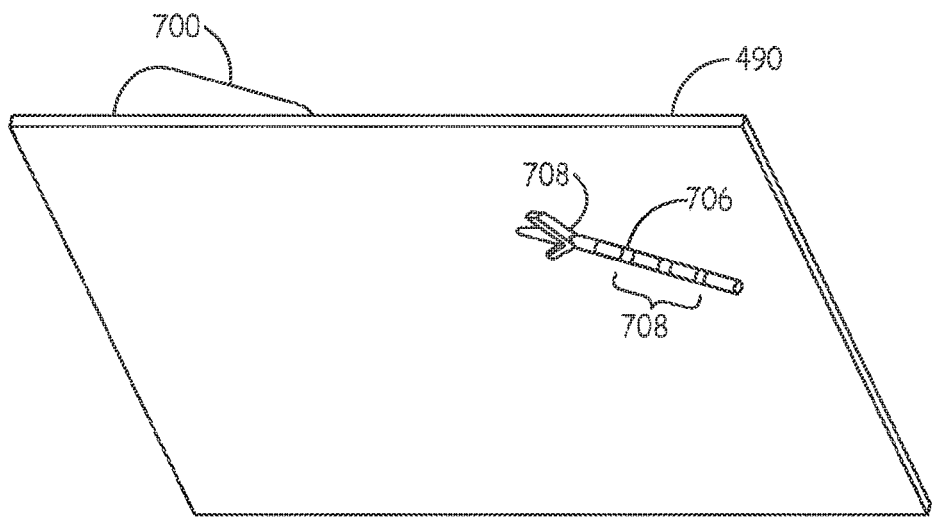
FIG. 30 is a perspective view of the IMD and lead of FIG. 26 after being deployed to an implant site using the implant tool of FIG. 29A.

FIG. 30 is a perspective view of IMD 700 and lead 706 after being deployed to an implant site using tool 750. Lead 706 extends through tissue layer 490 positioning electrodes 708 beneath tissue layer, in proximity to a targeted nerve. In this embodiment, lead 706 is shown to further include fixation tines 708. Fixation tines 708 may be flexible tines that are conformed along lead 706 when confined within second shaft portion 758 and expand to promote fixation of lead 706 beneath tissue layer 490. IMD 700 remains above tissue layer 490. In some applications, lead 706 and IMD 700 remain above layer 490, and tines 708 promote stable positioning of lead 706 along the tissue layer 490. The use of tool 750 enables implantation of IMD 700 and lead 706 and fixation of lead 706 in a single step. It is contemplated that other fixation members described above may be implemented with IMD 700 for anchoring IMD 700 to tissue layer 490.

Figure 31:
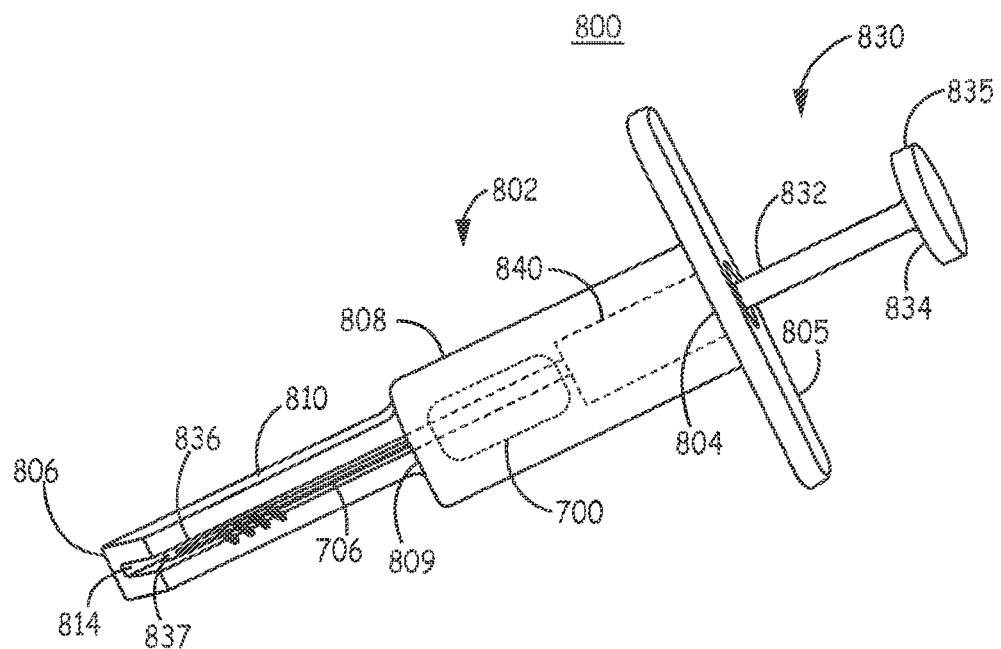
FIG. 31 is a perspective view of another exemplary embodiment of an implant tool that may be used to deploy an IMD and lead to a desired implant location in a minimally invasive procedure.

FIG. 31 is a perspective view of an another embodiment of an implant tool 800 that may be used to deploy IMD 700 and lead 706 to a desired implant location in a minimally invasive procedure. Implantation tool 800 includes a syringe body 802 and a plunger 830. Syringe body 802 extends from a proximal end 804 to a distal end 806. Distal end 806 may be a smooth or blunt end for applying to a tissue layer 490. Alternatively, distal end 806 may be a cutting or dissecting edge to cut through skin and/or dissect the IMD pocket. Proximal end 804 may include a stop surface 805 to interface with a plunger stop surface 834.

Syringe body 802 includes a distal needle guiding portion 810 extending proximally from the distal end 806 and a proximal IMD guiding portion 808 extending between proximal end 804 and distal needle guiding portion 810. The needle guiding portion 810 may define an open sided lumen 814.

IMD guiding portion 808 defines an inner lumen large enough to retain IMD 700 (indicated by dashed line). Plunger 830 extends between a proximal end 835 and a distal end 837 and includes a proximal shaft 832, a midportion 840 (enclosed within IMD guiding portion 808), and a distal hollow needle portion 836 extending through the open sided lumen 814 of distal needle guiding portion 810 of syringe body 802. Proximal end 835 includes a stopping interface 834 that enables a user to advance plunger 830 a controlled distance into syringe body 802. Distal end 837 is a sharpened tip of a distal hollow needle portion 836. Fixation lead 706 is loaded in hollow needle portion 836 and IMD 700 is loaded in IMD guiding portion 808, e.g. through distal opening 809 of IMD guiding portion 808.

Figure 32:
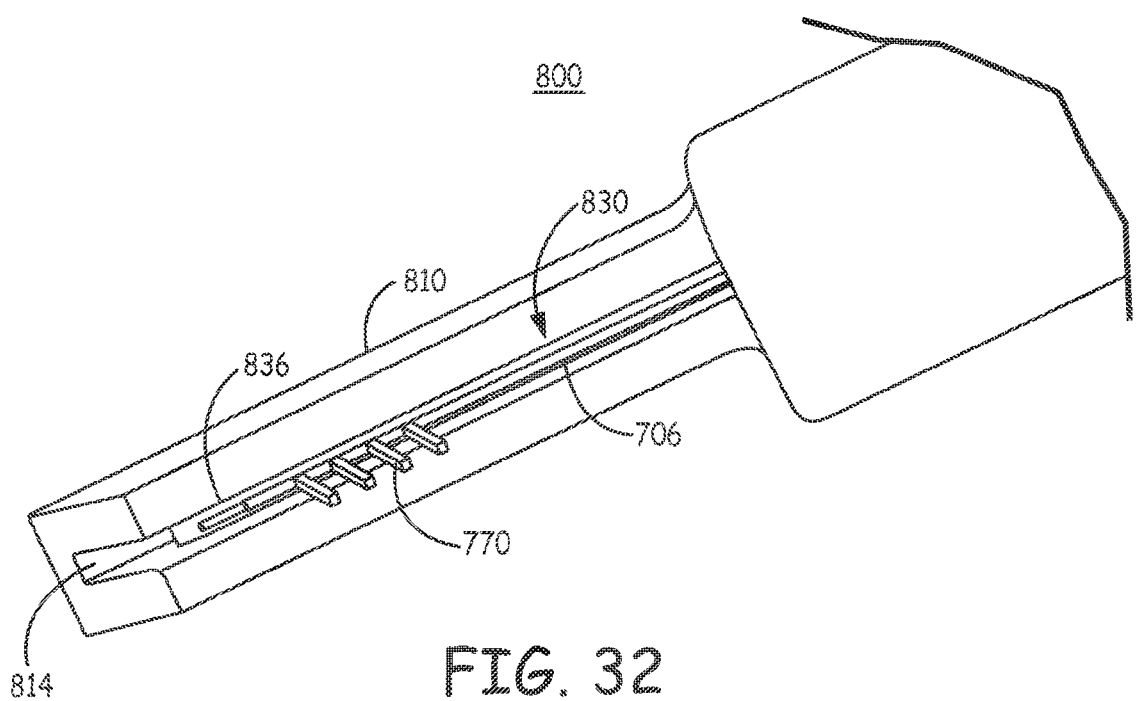
FIG. 32 is an enlarged perspective view of a distal portion of the implant tool of FIG. 31.

FIG. 32 is an enlarged perspective view of a distal portion of implant tool 800. Lead 706 is shown to include one or more fixation members 770 in the embodiment shown. Fixation members 770 may freely extend through slotted distal hollow needle portion 836 of plunger 830 and open sided lumen 814 of needle guiding portion 810.

Figure 33A:
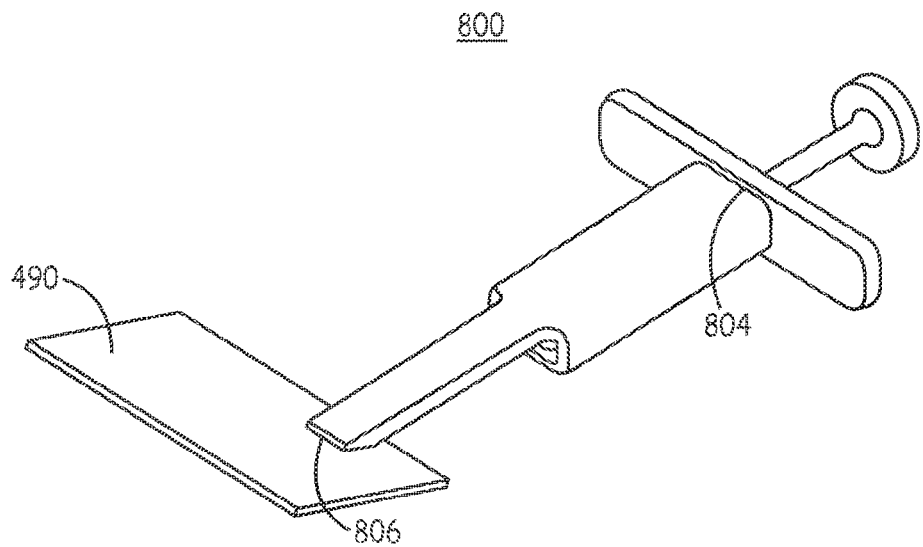
FIGS. 33a-33d show perspective views of an exemplary implant tool being used to deploy an IMD and lead to a desired implant site.

FIGS. 33a-33d show perspective views of implant tool 800 being used to deploy IMD 700 and lead 706 to a desired implant site. In FIG. 33a, implant tool distal end 806 is advanced to a desired implant location along tissue layer 490 by a user gripping syringe body proximal end 804. Distal end 806 may be a dissecting end that creates an IMD pocket through subcutaneous layers as it is advanced to tissue layer 490.

Figure 33B:
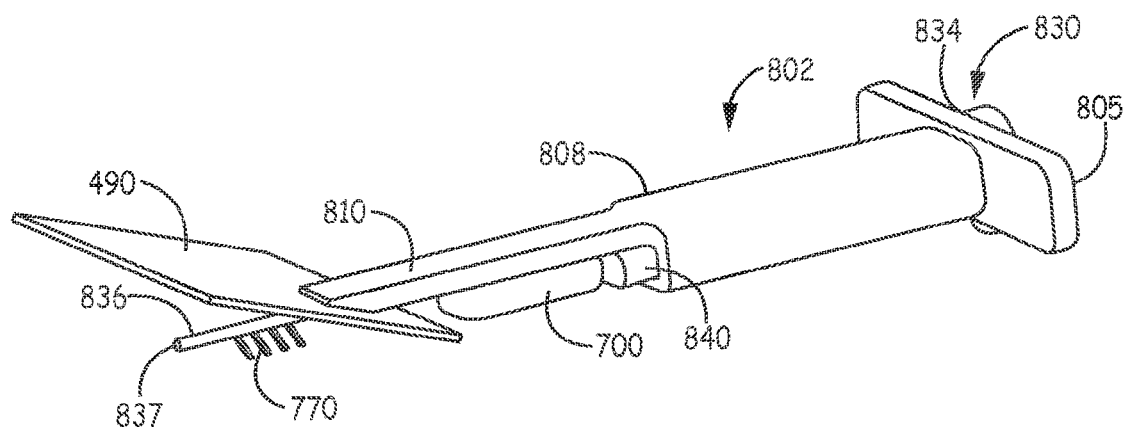

As shown in FIG. 33b, plunger 830 is advanced through syringe body 802 to simultaneously eject IMD 700 from IMD guiding portion 808 (by advancing plunger mid-portion 840) and pierce distal tip 837 of needle portion 836 through tissue layer 490 as needle portion 836 is advanced out of needle guiding portion 810. Distal tip 837 is advanced a maximum distance corresponding to the distance stopping interface 834 of plunger 830 travels before interfacing with stop surface 805 of syringe body 802. Tines 770 may flex inwardly during injection through tissue layer 490 than expand to resist retraction of lead 706 through tissue layer 490.

Figure 33C:
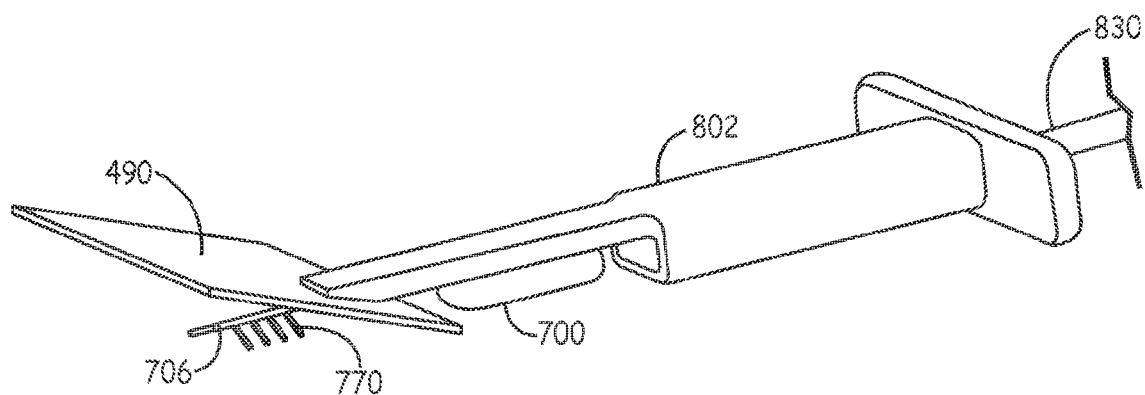
Figure 33D:
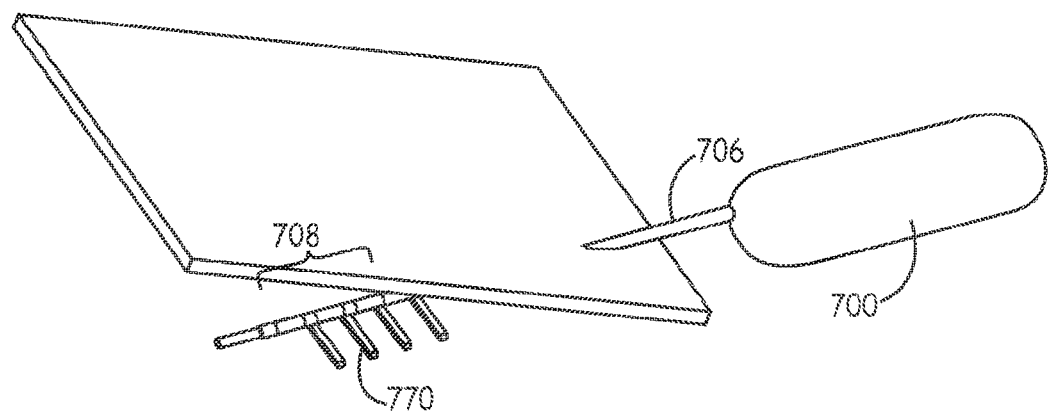

Plunger 830 is withdrawn from syringe body 802 as shown in FIG. 33c. IMD lead 706 is retained beneath tissue layer 490 by fixation members 770. Syringe body 802 may then be withdrawn leaving IMD 700 at a desired implant site over tissue layer 490 with tethered lead 770 extending through tissue layer 490. Electrodes 708 (FIG. 33d) are deployed to a targeted therapy delivery site in close proximity to a target nerve and passively anchored by tines 770. Additional fixation techniques may be used to anchor IMD 700 in place as described previously herein.

In this way, electrodes 708 can be positioned in close proximity to a nerve such as the tibial nerve without having to deliver stimulation pulses through a tissue layer such as the deep fascia. Placement beneath the tissue layer may reduce the pulse energy required for efficacious therapy. Only a small puncture through the deep fascia or other superficial tissue layer is required to position the electrodes 708 in close proximity to the tibial nerve and by extending lead 706 through the deep fascia, IMD 700 may also be stably anchored over the deep fascia.

Figure 34:
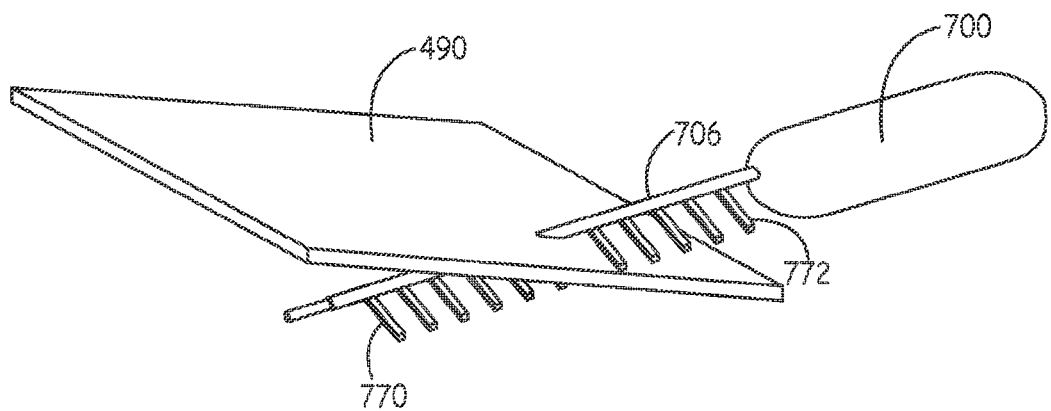
FIGS. 34 and 35 are perspective views of an alternative exemplary embodiment of an IMD and lead including distal fixation members and proximal fixation members.
Figure 35:
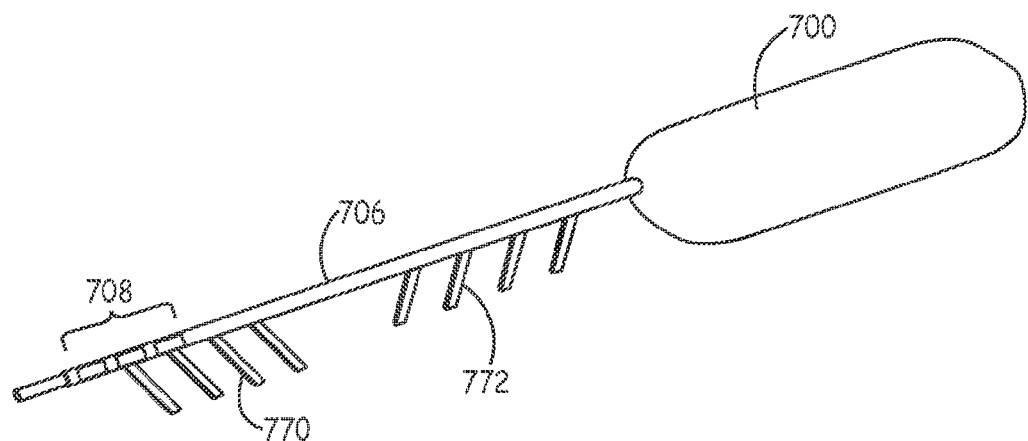

FIGS. 34 and 35 are perspective views of an alternative embodiment of IMD 700 and lead 706 in which lead 706 includes one or more distal fixation members 770 and one or more proximal fixation members 772. As shown in FIG. 34, distal fixation members 770 may be advanced through tissue layer 490 to reduce the likelihood of lead 706 migrating back through tissue layer 490. Proximal fixation members 772 reduce the likelihood of lead 706 migrating deeper, i.e. advancing further through tissue layer 490. As shown in FIG. 35, proximal fixation members 772 may extend from lead 706 at a different angle and/or direction than distal fixation members 770 to restrict movement of lead 706 in one direction while distal fixation members 770 restrict movement in a different opposite direction. It is contemplated that multiple fixation members may extend in multiple directions from lead 706 to limit movement of lead 706 and thereby fix lead 706 and electrodes 708 at a desired implant location.

Figure 36:
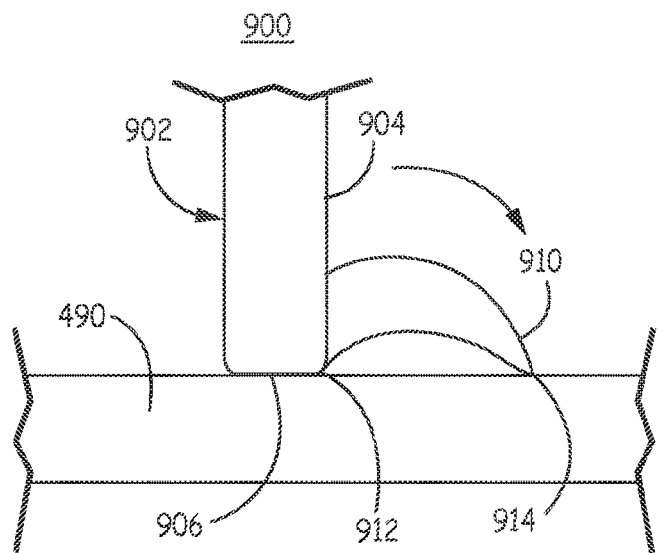
FIG. 36 is a side view of an exemplary IMD including a fixation member configured as a curved barb or hook.

FIG. 36 is a side view of IMD 900 including a housing fixation member configured as a curved barb or hook 910. Hook 910 extends between a proximal end 912 and distal free end 914. Proximal end 912 is attached to a bottom face 904 of IMD housing 902, at or along an intersection with a side wall 906 of housing 902. Distal end 914 is a pointed or sharpened tissue-penetrating tip. Hook 910 is positioned along housing 902 such that a side wall 906 of housing 902 can be positioned along a tissue surface, and, upon rotation of the IMD about an intersection between side wall 906 and bottom face 904, distal end 914 penetrates tissue layer 490 as bottom face 904 is laid against tissue layer 490.

Figure 37:
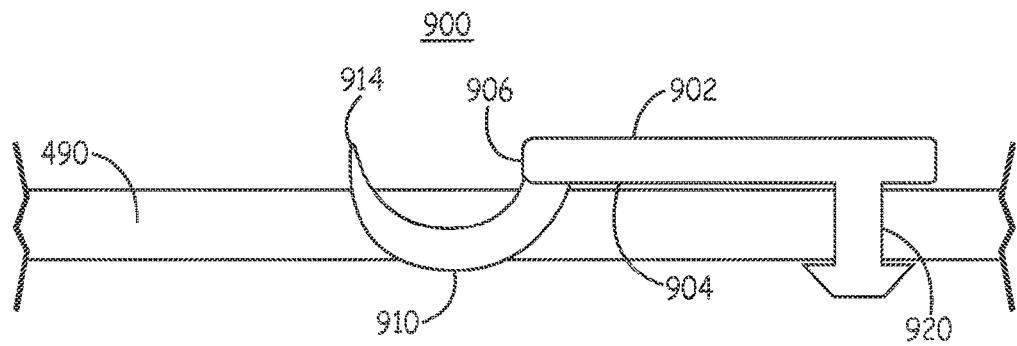
FIG. 37 is a side view of the IMD shown in FIG. 36 after fixation against a tissue layer.

FIG. 37 is a side view of IMD 900 after fixation against a tissue layer 490. Fixation member distal end 914 may fully penetrate through tissue layer 490 and curve back up through tissue layer 490 such that end 914 exits a top surface of tissue layer 490. Alternatively, fixation member distal end 914 may remain below or within tissue layer 490. IMD bottom face 904 is stably positioned against tissue layer 490. Hook 910 may include barbs or tines extending therefrom to further resist retraction of hook 910 through tissue layer 490.

IMD 900 may include a second fixation member 920 in some embodiments. A second fixation member 920 may extend from bottom face 904 or an IMD housing sidewall and be advanced through tissue layer 490 as bottom face 904 is rotated down and against tissue layer 490. In the embodiment shown, second fixation member 920 is embodied as a flanged post, e.g. corresponding to the fixation members 110 shown in FIGS. 3 and 4. Alternatively, a second fixation member may correspond to any of the fixation members, or adaptations or combinations thereof, described in conjunction with FIGS. 9-25. Fixation member hook 910 and/or fixation member 920 may additionally serve as or include an electrode for delivering a neurostimulation therapy and/or sensing electrophysiological signals.

Figure 38:
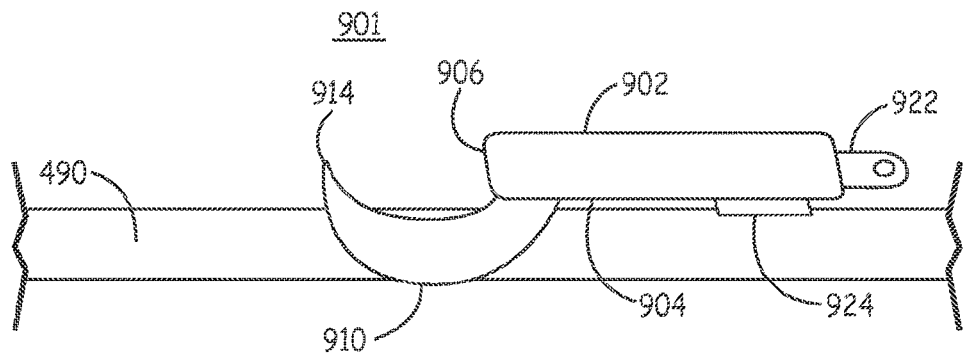
FIG. 38 is a side view of an alternative exemplary embodiment of an IMD including a fixation member hook.

FIG. 38 is a side view of an alternative embodiment of an IMD 901 including fixation member hook 910. IMD 901 includes a protruding tab 922 for facilitating a fixation member, which may be a suture or any of the other fixation members shown and described herein as extending through an aperture formed along a portion of an IMD housing.

IMD 901 further includes one or more electrodes 924 positioned along bottom face 904 of IMD housing 902. Upon rotation of IMD 901 against tissue layer 490 about an intersection between side wall 906 and bottom face 904, hook 910 will penetrate tissue layer 490 and anchor bottom face 904 and electrode(s) 924 against tissue layer 490. Electrode(s) 924 are positioned to deliver neurostimulation through tissue layer 490, to a nerve extending beneath tissue layer 490, e.g. the tibial nerve extending beneath a deep fascia layer. In some embodiments, hook 910 may serve as or include an electrode. Accordingly, hook 910 and electrode 924 may form a bipolar pair for delivering neurostimulation. Fixation of IMD 901 and electrode placement are performed simultaneously.

FIG. 39A is a side view of an IMD 950 including one or more electrodes 962 and 964 embodied as feedthrough pins extending from IMD housing 952. Distal ends 963 and 965 of feedthrough pin electrodes 962 and 964 may extend through a tissue layer 490 to position electrodes 962 and 964 in closer proximity to a targeted nerve. A feedthrough pin electrode 964 may extend at an acute angle relative to a face of housing 952 to promote anchoring of the IMD 950 at the implant site. A distal end 963 of a feedthrough electrode 962 may be enlarged or flattened to provide a greater electrode surface area and/or a retention member to promote IMD fixation.

A feedthrough assembly 970 is shown in FIG. 39B. Feedthrough assembly 970 includes a flanged ferrule 972, an insulator 974, and a feedthrough pin 976. The ferrule 972 is bonded or welded within an aperture of the IMD housing. The insulator 974, which may be glass, sapphire or ceramic, is bonded to ferrule 972, for example using a glass seal, a gold braze, or a diffusion bond. An electrically conductive feedthrough pin 976 extends through insulator 974 and may be bonded to insulator 974 using a glass seal, gold braze or diffusion bond or other sealed joint. Feedthrough pin 976 may be used as a therapy delivery electrode, eliminating additional interconnects, conductors, and electrode components. All or a portion of feedthrough pin 976 may be coated with an electrode surface enhancing material, such as titanium, platinum, iridium, or alloys thereof, to increase electrode surface area and/or enhance electrochemical stability of the electrode. The feedthrough pin 976 may be stamped to form a flattened distal end, e.g. nail head or paddle shaped, to increase the stimulating surface area.

FIG. 40 is an enlarged perspective view of a feedthrough pin 980 including a stamped distal end 982 forming a "nail head" geometry, which increases electrode surface area and may act as a fixation member flange to promote anchoring of an associated IMD at an implant site.

FIG. 41 is a depiction of a variety of stamped or preformed feedthrough pins including variously shaped distal ends that may be implemented to increase electrode surface area and/or promote fixation of the IMD at an implant site. A looped distal end 990, a hooked distal end 991, a triangular distal end 992, an angled distal end 993, a helical distal end 994, and paddle shaped distal ends 995, 996 are shown.

Figure 42:
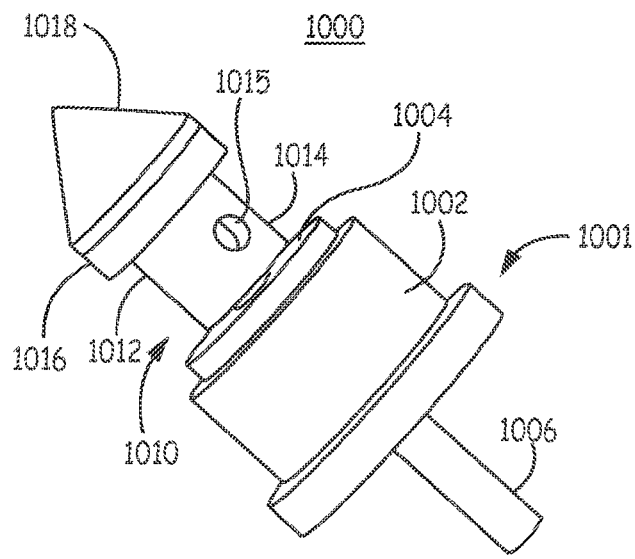
FIG. 42 is a perspective view of an exemplary fixation member electrode and feedthrough assembly.

FIG. 42 is a perspective view of a fixation member electrode and feedthrough assembly 1000. Assembly 1000 includes an insulated electrical feedthrough 1001 and a fixation member 1010. Feedthrough 1001 includes a ferrule 1002 bonded to an insulator 1004 and a feedthrough pin 1006 extending through the insulator 1004. The ferrule 1002 is configured to be welded within an aperture of and IMD housing.

Fixation member 1010 may be coupled to insulator 1004, e.g. by brazing, diffusion bonding, or glass sealing methods. Fixation member 1010 includes a flanged hollow post 1012. Feedthrough pin 1006 extends through post 1012, which may include an aperture 1015 for facilitating welding of post 1012 and feedthrough pin 1006. Aperture 1015 may be sealed, e.g. backfilled with medical adhesive, after welding.

Post proximal end 1014 is fixedly mounted on insulator 1004 and flanged distal end 1016 may be positioned against tissue for delivering stimulation energy. As described previously in conjunction with FIGS. 3 and 4, fixation member 1010 may include sharpened puncture tip 1018 extending from flanged distal end 1016 for puncturing through a tissue layer for fixation of an associated IMD. Flanged distal end 1016 promotes fixation of IMD when a tissue layer is captured between flanged distal end 1016 and a face of the IMD. Puncture tip 1018 may be a bioabsorbable or dissolvable material as described previously herein such that it is absorbed over time, leaving flanged post 1012 behind to serve as both a fixation member and electrode. By electrically coupling feedthrough pin 1006 directly to fixation member 1012, additional conductors, interconnects and electrode components are eliminated.

Figure 43:
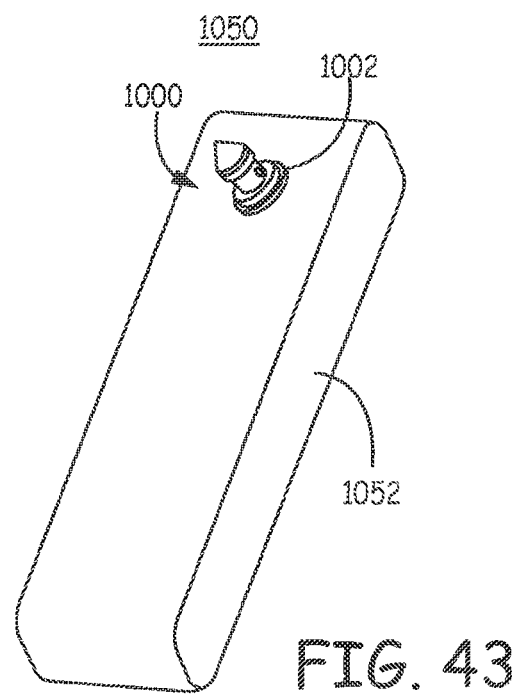
FIG. 43 is a bottom perspective view of an IMD including the fixation member electrode and feedthrough assembly of FIG. 42.

FIG. 43 is a bottom perspective view of an IMD 1050 including the fixation member electrode and feedthrough assembly 1000 of FIG. 42. The assembly 1000 may be coupled to the IMD housing 1052 by welding ferrule 1002 into an aperture formed at any desired location along IMD housing 1052. By implementing a fixation member electrode and feedthrough assembly 1000, manufacturing techniques may be simplified or reduced in cost by eliminating additional steps and components needed to separately assemble an electrode, fixation member and feedthrough assembly. Miniaturization and ease of use are promoted by eliminating device components and enabling fixation and electrode placement in a single step.

Figure 44:
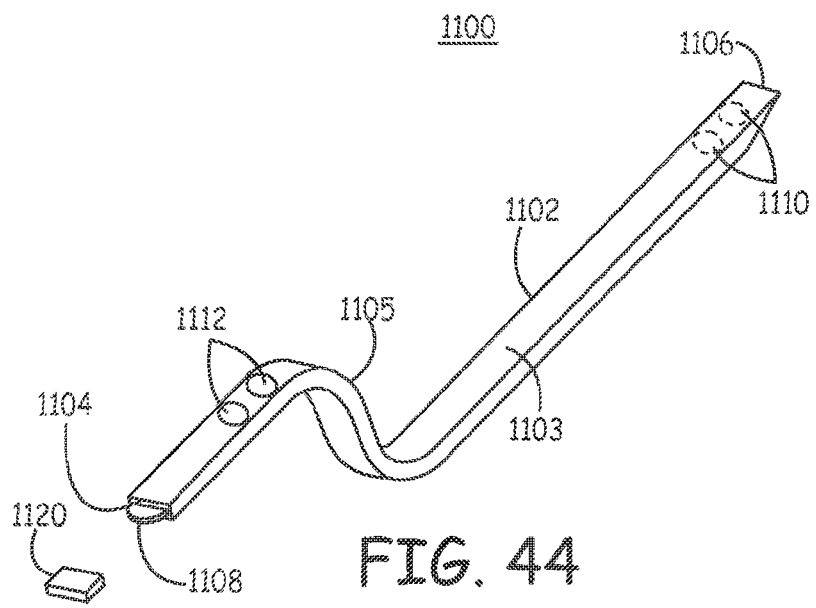
FIG. 44 is a perspective view of an exemplary implant tool for use in a minimally invasive IMD implantation procedure.

FIG. 44 is a perspective view of an implant tool 1100 for use in a minimally invasive IMD implantation procedure. To gain access to a targeted implant site, such as the tibial nerve, a miniaturized IMD is advanced through a small skin incision and into a tissue pocket, e.g. superior to the flexor retinaculum and posterior to the medial malleolus. The target location for an IMD with electrodes incorporated along an IMD housing may be approximately 5 cm (or less) above the medial malleolus, with the device adjacent to the retinaculum, providing stimulation therapy through a deep fascia layer.

Implant tool 1100 includes a body 1102 extending between a first end 1104 and a second end 1106. The first end 1104 is provided with an incising blade 1108 for cutting an incision through the skin. Incising blade 1108 may be configured as a retractable blade or removable blade. Alternatively, a cover or blade guard 1120 may be provided to cover and protect the blade 1108 when not in use. When configured as a retractable blade, a slide, lever, spring or other actuating mechanism for retracting and advancing blade 1108 may be positioned along body 1102, e.g. near second end 1106. The blade 1108 has a width to create an incision that is not wider than required for inserting the IMD. In one embodiment, the blade width is provided to be approximately equal to the incision width needed to insert the IMD.

The second end 1106 includes a blunt edge for performing dissection down to and along a tissue plane, e.g. along the deep fascia, for forming a tissue pocket in which an IMD will be positioned. The tool body 1102 may include graduations, markings, physical protrusions, stops or other features for indicating a depth of a tissue pocket that has been created, enabling a pocket of adequate depth and proper width to be formed for receiving the IMD.

Tool body 1102 includes a straight portion 1103 and an S-shaped bend 1105 as shown such that first end 1104 extends approximately parallel to straight portion 1103. Second end 1106 extends from straight portion 1103. However it is recognized that tool body 1102 may include one or more bends, curves or angles to provide ergonomic, comfortable use of tool 1100 and to position ends 1104 and 1106 at desired angles relative to tool body 1102 to facilitate incising and dissection during an implant procedure.

In some embodiments, implant tool 1100 includes nerve locating electrodes 1110 along a bottom surface of the tool body 1102, near the blunt, dissecting end 1106. As end 1106 is advanced along a tissue plane, electrodes 1110 may be used to deliver test pulses until a location is identified which results in a satisfactory neurostimulation response. A satisfactory response to stimulation may be identified based on a stimulation threshold, an EMG signal, accelerometer or other motion signal, other physiological signal or user observation.

Electrodes 1110 may be electrically coupled to an external pulse generator via contacts 1112 positioned along tool body 1102 near first tool end 1104. Contacts 1112 may be snaps, pads or sockets to facilitate connection of cables, e.g. with alligator clips, extending to an external stimulation pulse generator. Contacts 1112 may each be coupled to respective insulated conductors extending through or along tool body 1102 to respective electrodes 1110. Alternatively conductor wires may be incorporated in tool 1100 and extend away from tool 1100 for connecting to a pulse generator.

Electrodes 1110 may be positioned a distance from end 1106 and sized and spaced from each other to correspond to electrodes along an IMD housing or IMD lead such that stimulation testing can be performed in a manner that simulates stimulation energy being delivered by the IMD electrodes or lead electrodes that will be used in the implanted system. While only two electrodes 1110 are shown, it is recognized that multiple electrodes 1110 may be provided along tool body 1102, with a corresponding number of connectors 1112, to enable testing of multiple electrode combinations and electrode locations without having to reposition tool 1100.

Once an optimal implant location is identified based on measured or observed responses to test stimulation pulses, tool 1100 may be removed and an IMD is inserted into the created tissue pocket at the identified depth using a delivery tool. Alternatively, tool 1100 may be left in place as a guide for inserting and locating the IMD at the desired implant site.

Figure 45:
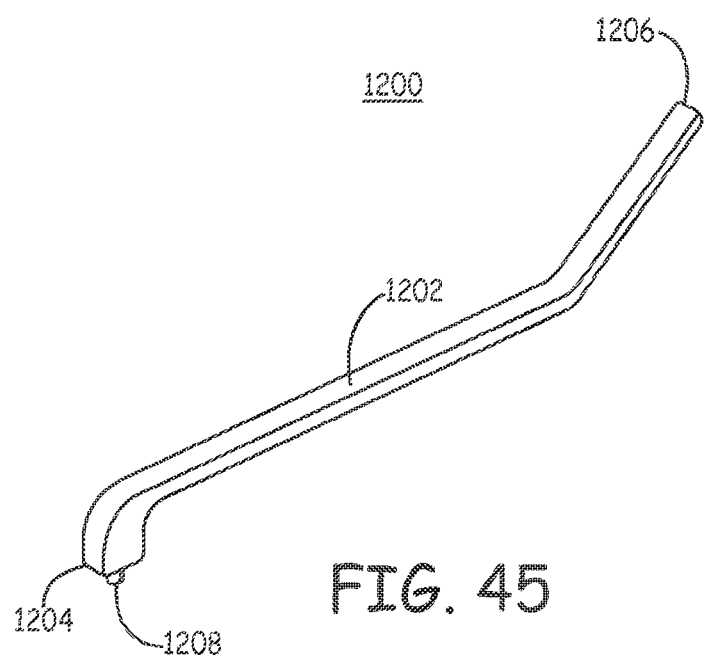
FIG. 45 is a perspective view of an alternative exemplary embodiment of an implant tool.

FIG. 45 is a perspective view of an alternative embodiment of an implant tool 1200. Tool 1200 includes a tool body 1202 extending between a first end 1204 and a second end 1206. First end 1204 includes an incising blade 1208, which may be retractable, removable, or covered by a blade guard as described above, and is used for creating a minimally sized skin incision for implanting an IMD. Second end 1206 includes a blunt dissecting edge for advancing through tissue and creating a tissue pocket along a desired tissue layer. While not shown in FIG. 45, tool 1200 may additionally include electrodes and associated connectors for nerve location and graduations or other markings or features for identifying a depth of a created tissue pocket.

First end 1204 is shown angled approximately ninety degrees from tool body 1202 and second end 1206 is shown angled approximately forty-five degrees from tool body 1202. As described above, numerous configurations of tool body 1202 may be conceived which provide comfortable handling of tool 1200 and facilitate tissue pocket creation at a desired IMD implant site. For example, ease of use and access to a desired implant site may be promoted by implementing particular relative angles between opposing dissecting and incising ends, relative to each other or to a central tool body extending there between. In some embodiments, the shape of tool body 1202 is adjustable, e.g. when formed of a malleable material.

Figure 46:
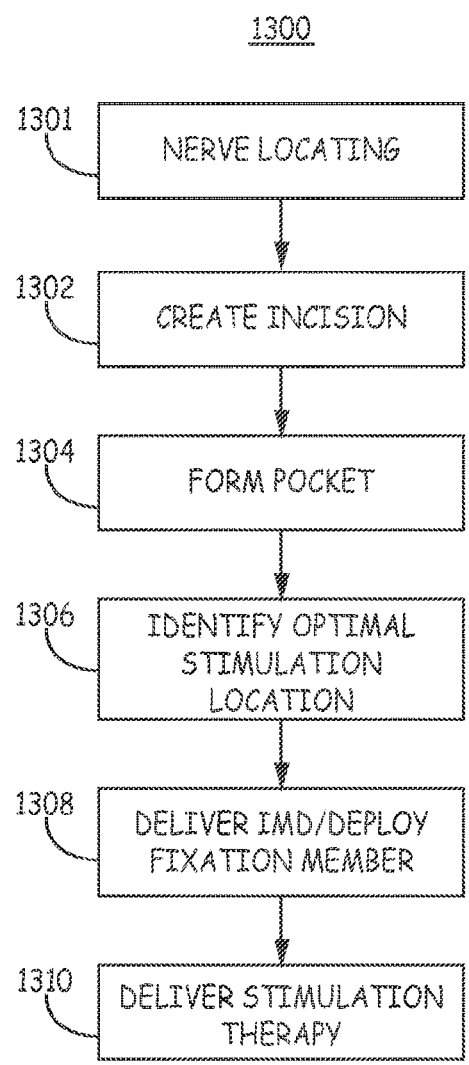
FIG. 46 is a flow chart of an exemplary method for delivering a neurostimulation therapy.

FIG. 46 is a flow chart 1300 of a method for delivering a neurostimulation therapy according to one embodiment. An optional initial step is performed at block 1301 to locate or visualize a targeted nerve, such as the tibial nerve. The location of the tibial nerve, for example, may be performed using ultrasound, external skin electrodes, or other imaging or stimulating techniques. Visualization or localization of the tibial nerve, or another targeted neural site, as an initial step can be used to guide a clinician in selecting an incision site.

At block 1302, a skin incision is created. A skin incision may be created using a standard scalpel or an incising edge or blade of an implant tool as described above, for example in conjunction with FIGS. 44 and 45. The skin incision is minimized in size to accommodate a miniaturized IMD. For example the length of the skin incision may be made approximately equal to a width of an incising end of an implant tool to provide an incision just large enough for insertion of an IMD or an IMD delivery tool.

At block 1304, a tissue pocket is formed for receiving the IMD along a tissue plane at a desired implant site. The tissue pocket may be dissected using a dissecting end of implant tool as described in conjunction with FIGS. 44 and 45. Using an appropriately sized tool, the pocket is formed to be just large enough to receive the IMD (or a delivery tool used to deploy the IMD). The tissue pocket is formed along a superficial surface of a tissue layer, for example a superficial surface of the deep fascia that is superficial to a targeted nerve, for positioning the IMD along the superficial surface.

An optimal stimulation location may be identified at block 1306 prior to deploying the 1 MB. Electrodes included on an implant tool or on an IMD delivery tool advanced into the created pocket may be used to identify the optimal stimulation location by delivering test stimulation pulses and measuring and/or observing a stimulation response. In some embodiments, electrodes included on the 1 MB housing or a lead coupled to the 1 MB may be exposed through an 1 MB delivery tool and can be used for delivering test pulses from the IMD to test different IMD locations prior to fixing the IMD at an implant site.

Once an optimal implant location is identified, the IMD is delivered to the implant site at block 1308. The IMD may be delivered to the implant site using a delivery tool as described herein to simultaneously deliver the IMD and deploy a fixation member to anchor the IMD at the implant site. Alternatively, a fixation member may be deployed in a separate step after positioning the IMD, which may include verifying efficacious stimulation by the IMD prior to fixation. Fixation of the IMD may include the use of passive and/or active fixation members, such as tines or other passive fixation members extending from the IMD housing and/or from an electrical lead extending from the IMD. In some examples, an IMD incorporating electrodes along the IMD housing is positioned along the superficial tissue surface and passively fixated by tines or other passive fixation members extending from the IMD housing. In other examples, an IMD incorporating electrodes along the IMD housing and/or incorporated in active housing fixation members is positioned along the superficial surface of the tissue layer and the active housing fixation members extend into the tissue layer. An active fixation member may extend into the tissue layer that is superficial to the targeted nerve to capture the tissue layer between a portion of the active fixation member and the IMD housing. In some embodiments described herein, an active fixation member extends through an aperture of the IMD housing. Any of the fixation techniques described herein may be used to anchor the IMD at a desired site.

In still other examples, delivering the IMD to the implant site may include concomitantly delivering a lead coupled to the 1 MB. The lead may extend along the superficial surface of the tissue layer or be inserted into the tissue layer to both fix the IMD at the therapy delivery site and position electrodes carried by the lead near the targeted nerve.

In various embodiments, electrodes for delivering neurostimulation energy may be carried along the IMD housing, incorporated in or along a fixation member, and/or carried by a lead extending from the IMD. Delivery of the 1 MB system and fixation of the 1 MB system can be performed simultaneously in a single step. After implanting and fixating the IMD system, the skin incision is closed.

At block 1310, the IMD is enabled to deliver a neurostimulation therapy according to a prescribed protocol. Depending on the particular IMD configuration being used, the neurostimulation therapy is delivered through a tissue layer, e.g. through a deep fascia layer, using electrodes positioned above (superficially to) the tissue layer to stimulate a relatively deeper nerve extending beneath the tissue layer. In one embodiment, the tibial nerve is stimulated through the deep fascia tissue layer by wholly implanted electrodes positioned superficially to the deep fascia, i.e. on the opposing side of the deep fascia, from the nerve and superior to the flexor retinaculum. In other embodiments, electrodes may be positioned in close proximity to a targeted nerve by advancing the electrodes, which may additionally be configured as fixation members as described herein, through an overlying tissue layer, e.g. a deep fascia layer.

Thus, various embodiments of a minimally invasive IMD system have been presented in the foregoing description with reference to specific embodiments, as well as methods for implanting and securing the same. The various features of IMD fixation members and implant tools and associated methods of use described herein may be implemented in any combination other than the particular combinations shown in the illustrative embodiments, which may include adding or omitting some features. It is appreciated that various modifications to the referenced embodiments may be made without departing from the scope of the disclosure as set forth in the following claims.

The invention claimed is:

1. A device for delivering a neuromodulation therapy, comprising:
   an implantable medical device configured to be implanted on a surface of a tissue layer superficial to a tibial nerve of a patient, the implantable medical device comprising:
     a housing;
     at least one fixation member coupled to the housing, the at least one fixation member configured to engage the tissue layer and secure the implantable medical device at an implant site;
     a plurality of electrodes; and
     a pulse generating circuit enclosed in the housing and coupled to the plurality of electrodes, the pulse generating circuit configured to generate stimulation pulses for delivery as electrical stimulation therapy via the plurality of electrodes to the nerve through the tissue layer,
     wherein at least one of the plurality of electrodes is located on an exterior surface of the housing configured to contact the tissue layer superficial to the tibial nerve of the patient when the implantable medical device has been implanted at the implant site, and
     wherein the at least one fixation member comprises a flexible material configured to allow the at least one fixation member to assume a first position when the implantable medical device is received in an implantation tool and to extend to a second position when expelled from the implantation tool to engage the tissue layer at the implant site.

2. The device of claim 1, wherein the at least one fixation member includes a plurality of tines.

3. The device of claim 2, wherein each of the plurality of tines includes a descending portion extending away from the housing to a distal end, the distal end comprising a sharpened tip configured to penetrate the tissue layer.

4. The device of claim 1, wherein the at least one fixation member is formed of a material comprising nitinol.

5. The device of claim 1, wherein the at least one fixation member comprises a shape memory material configured to allow the at least one fixation member to bend to a flared position as the second position when advanced into the tissue layer to resist movement out of the tissue layer.

6. The device of claim 1, wherein the at least one fixation member comprises a feedthrough pin including a distal end comprising a feedthrough pin electrode, the feedthrough pin configured to extend through the tissue layer at the implant site to position the feedthrough pin electrode in proximity to the nerve of the patient.

7. The device of claim 1, wherein the at least one fixation member comprises a curved hook extending away from the housing to a distal end of the hook, the distal end of the hook comprising a sharpened tip configured to penetrate the tissue layer at the implant site to secure the implantable medical device.

8. The device of claim 1, wherein the at least one fixation member comprises a first fixation member that extends away from the housing in a first direction and a second fixation member that extends away for the housing in a second direction that is different from the first direction.

9. The device of claim 1, wherein the at least one fixation member extends through one or more lumens positioned at one or more anchoring locations along the exterior of the housing, the at least one fixation member configured to be held in the first position when received in the implantation tool and to assume the second position when advanced out of the implantation tool.

10. A system for delivering a neuromodulation therapy, comprising:
    an implantable medical device configured to be implanted on a surface of a tissue layer superficial to a tibial nerve of a patient, the implantable medical device comprising:
      a housing,
      at least one fixation member coupled to the housing, the at least one fixation member configured to engage the tissue layer and secure the implantable medical device at an implant site,
      a plurality of electrodes, and
      a pulse generating circuit enclosed in the housing and coupled to the plurality of electrodes, the pulse generating circuit configured to generate stimulation pulses for delivery as electrical stimulation therapy via the plurality of electrodes to the nerve through the tissue layer,
      wherein at least one of the plurality of electrodes is located on an exterior surface of the housing configured to contact the tissue layer superficial to the tibial nerve of the patient when the implantable medical device has been implanted at the implant site; and an implantation tool configured for use in implanting the implantable medical device at the implant site, the implantation tool comprising:
  a body comprising an inner lumen configured to receive the implantable medical device and the at least one fixation member within an inner lumen of the body so that the fixation member is held in a first position when confined within the inner lumen, the body comprising a distal end comprising a tip configured to allow the distal end of the body to be positioned at the implant site, and
  a plunger configured to be received in and extend through at least a portion of the body and to engage the implantable medical device, the plunger configured to be advanced into the inner lumen to eject the at least one fixation member from the distal end of the body at the implant site so that the at least one fixation member assumes a flared position and engages the tissue layer to secure the implantable medical device at the implant site,
  wherein the at least one fixation member comprises a flexible material configured to allow the at least one fixation member to assume a first position when the implantable medical device is received in the implantation tool and to extend to a second position when expelled from the implantation tool to engage the tissue layer at the implant site.

11. The system of claim 10, wherein the at least one fixation member includes a plurality of tines.

12. The system of claim 11, wherein each of the plurality of tines includes a descending portion extending away from the housing to a distal free end, the distal free end comprising a sharpened tip configured to penetrate the tissue layer.

13. The system of claim 10, wherein the at least one fixation member is formed of a material comprising nitinol.

14. The system of claim 10, wherein the at least one fixation member is formed of a material having shape memory material configured to allow the at least one fixation member to bend to a flared position as the second position when advanced into the tissue layer to resist movement out of the tissue layer.

15. The system of claim 10, wherein the tip at the distal end of the body of the implantation tool comprises a cutting edge configured to cut through skin of the patient.

16. The system of claim 10, wherein at least one of the plurality of electrodes is located on the exterior surface of the housing and is configured to contact the tissue layer when the implantable medical device has been implanted at the implant site.

17. The system of claim 10, wherein the implantation tool is configured to perform delivery and fixation of the implantable medical device simultaneously as the implantable medical device is expelled from the implantation tool at the implant site.

18. The system of claim 10, wherein the implantation tool comprises nerve locating electrodes configured to be advanced toward one or more implant sites, to deliver test stimulation pulses and measure a stimulation response to the test stimulation pulses to identify a nerve location.

19. The system of claim 10, further comprising an external device for transmitting power from a position over the implantable medical device for powering the pulse generating circuit to generate stimulation pulses delivered to the nerve via the plurality of electrodes.

20. A method comprising:
receiving an implantable medical device within an inner lumen of a body of an implantation tool, the implantation tool configured to implant the implantable medical device at an implant site superficial to a nerve of a patient, the implantable medical device comprising:
  a housing;
  at least one fixation member coupled to the housing, the at least one fixation member configured to engage a tissue layer of the patient and secure the implantable medical device at an implant site;
  a plurality of electrodes; and
  a pulse generating circuit enclosed in the housing and coupled to the plurality of electrodes, the pulse generating circuit configured to generate stimulation pulses for delivery as electrical stimulation therapy via the plurality of electrodes to the nerve through the tissue layer,
  wherein at least one of the plurality of electrodes is located on an exterior surface of the housing configured to contact the tissue layer when the implantable medical device has been implanted at the implant site, and
  wherein the at least one fixation member comprises a flexible material configured to allow the at least one fixation member to assume a first position when the implantable medical device is received in an implantation tool and to extend to a second position when expelled from the implantation tool to engage the tissue layer at the implant site;
positioning a distal end of the implantation tool at the implant site; and
expelling the implantable medical device from the implantation tool to secure the implantable medical device at the implant site to allow the at least one fixation member to extend to the second position when expelled from the implantation tool to engage the tissue layer at the implant site.

21. The method of claim 20, wherein the at least one fixation member includes a plurality of tines.

22. The method of claim 21, wherein each of the plurality of tines includes a descending portion extending away from the housing to a distal end, the distal end comprising a sharpened tip configured to penetrate the tissue layer.

23. The method of claim 20, wherein the at least one fixation member is formed of a material comprising nitinol.

24. The method of claim 20, wherein the at least one fixation member is formed of a material having shape memory material configured to allow the at least one fixation member to bend to a flared position as the second position when advanced into the tissue layer to resist movement out of the tissue layer.

25. The method of claim 20, further comprising:
delivering, by the plurality of electrodes, the electrical stimulation therapy to the nerve through the tissue layer.

26. The method of claim 20, further comprising:
delivering, by nerve locating electrodes of the implantation tool, a set of test stimulation pulses to one or more implantation sites;
measuring, using electrical circuitry, a stimulation response to the set of test stimulation pulses to identify a selected implant site; and
expelling, using the implanting tool, the implantable medical device to implant the implantable medical device at the selected implant site.

* * * * *